US008071555B2

(12) United States Patent
Zhang et al.

(10) Patent No.: US 8,071,555 B2
(45) Date of Patent: Dec. 6, 2011

(54) PROTECTIVE SKIN CARE PEPTIDES

(75) Inventors: Lijuan Zhang, Kenmore, WA (US);
Scott M. Harris, Seattle, WA (US);
Timothy J. Falla, Woodinville, WA (US)

(73) Assignee: Helix BioMedix Inc., Bothell, MA (US)

( * ) Notice: Subject to any disclaimer, the term of this patent is extended or adjusted under 35 U.S.C. 154(b) by 607 days.

(21) Appl. No.: 12/290,236

(22) Filed: Oct. 28, 2008

(65) Prior Publication Data

US 2009/0142280 A1 Jun. 4, 2009

Related U.S. Application Data

(60) Provisional application No. 61/000,815, filed on Oct. 29, 2007.

(51) Int. Cl.
*A61K 38/06* (2006.01)
*A61K 9/00* (2006.01)
(52) U.S. Cl. ............... 514/21.9; 530/330; 424/78.06
(58) Field of Classification Search ............... None
See application file for complete search history.

(56) References Cited

U.S. PATENT DOCUMENTS

| 5,464,820 A | 11/1995 | Burton et al. ............... 514/16 |
| 5,763,576 A | 6/1998 | Powers ........................ 530/330 |
| 5,770,568 A | 6/1998 | Auerswald et al. ........... 514/12 |
| 6,096,327 A | 8/2000 | Lezdey et al. ............... 424/401 |
| 6,143,742 A | 11/2000 | Fuisz ........................ 514/231.5 |
| 6,211,155 B1 | 4/2001 | Dussourd et al. ............ 514/18 |
| 6,262,021 B1 | 7/2001 | Uvnas-Moberg et al. ...... 514/11 |
| 6,284,802 B1 | 9/2001 | Bissett et al. ............... 514/739 |
| 6,294,181 B1 | 9/2001 | Lezdey ....................... 424/400 |
| 6,319,907 B1 | 11/2001 | Ferguson ..................... 514/44 |
| 6,344,189 B1 | 2/2002 | Bunn et al. ................. 424/78.06 |
| 6,492,326 B1 | 12/2002 | Robinson et al. ............. 514/2 |
| 6,537,968 B1 | 3/2003 | Lezdey et al. ............... 514/12 |
| 6,962,904 B1 | 11/2005 | Sandberg et al. ............ 514/16 |
| 6,967,023 B1 | 11/2005 | Eini et al. .................. 424/401 |
| 6,974,799 B2 | 12/2005 | Lintner ....................... 514/18 |
| 7,041,506 B2 | 5/2006 | Campbell et al. ............. 435/402 |
| 7,238,656 B2 | 7/2007 | Wormser ....................... 514/2 |
| 7,265,097 B2 | 9/2007 | Kydonieus et al. ............ 514/55 |
| 7,271,239 B2 | 9/2007 | Bobek ........................ 530/327 |
| 2003/0175745 A1 | 9/2003 | Dean et al. ................... 435/6 |
| 2004/0009911 A1 | 1/2004 | Harris et al. ............... 514/12 |
| 2004/0167072 A1 | 8/2004 | Aggarwal et al. ............ 514/12 |
| 2005/0085422 A1 | 4/2005 | Georgiades et al. ........... 514/13 |
| 2005/0288229 A1 | 12/2005 | Sindrey et al. ............. 514/16 |
| 2006/0046271 A1 | 3/2006 | Hallahan ...................... 435/7.1 |
| 2007/0021347 A1 | 1/2007 | Khan et al. ................... 514/16 |
| 2007/0077305 A1 | 4/2007 | Le et al. ...................... 424/488 |
| 2007/0166267 A1 | 7/2007 | Majewski et al. .......... 424/70.14 |
| 2007/0183970 A1 | 8/2007 | Goldenberg et al. ........ 424/1.49 |
| 2007/0224150 A1 | 9/2007 | Chung ....................... 424/70.14 |

FOREIGN PATENT DOCUMENTS

| CA | 2276542 | 12/2000 |
| DE | 102004050563 A1 | 4/2006 |
| EP | 0858808 A2 | 8/1998 |
| EP | 1004595 A2 | 5/2000 |
| EP | 1 634 576 A1 | 3/2006 |
| EP | 1 815 843 A2 | 8/2007 |
| GB | 1357121 | 6/1974 |
| WO | WO 89/10099 A1 | 11/1989 |
| WO | WO 95/28832 A1 | 11/1995 |
| WO | WO 00/43417 A1 | 7/2000 |
| WO | WO 02/079408 A2 | 10/2002 |
| WO | WO 02/092623 A1 | 11/2002 |
| WO | WO 2006/042625 A2 | 4/2006 |
| WO | WO 2006/053688 A1 | 5/2006 |
| WO | WO 2006/108963 A1 | 10/2006 |
| WO | WO 2007/098255 A2 | 8/2007 |
| WO | WO 2007/098255 A3 | 8/2007 |

OTHER PUBLICATIONS

Kassem, 1996, Journal of Bone and Mineral Research, 11, 193-199.*
Herberts, 2003, Molecular Immunology, 39, 567-575.*
Cecile, 2000, Eur. J. Immunol., 30, 1172-1181.*
Schultz et al., Extracellular matrix: review of its roles in acute and chronic wounds, *World Wide Wounds* (www.worldwidewounds.com) (Aug. 2005).
Katayama et al., A pentapeptide from type I procollagen promotes extracellular matrix production, *Journal of Biological Chemistry* 268:9941-9944 (1993).
Greenbaum et al., Chemical approaches for functionally probing the proteome, *Molecular and Cellular Proteomics* 1:60-68 (2002).
Krstenansky et al., Probing proteinase active sites using oriented peptide mixture libraries—ADAM-10, *Letters in Drug Design and Discovery* 1:6-13 (2004).
Tran et al., Extracellular matrix signaling through growth factor receptors during wound healing, *Wound Repair and Regeneration* 12:262-268 (2004). Maquart et al., [Regulation of cell activity by the extracellular matrix: the concept of matrikines], *Journal de la Société de biologie* 193:423-428 (1999) Abstract Only.
Duca et al., Elastin as a matrikine, *Critical Reviews in Oncology/Hematology* 49:235-244 (2004).
Arul et al., Biotinylated GHK peptide incorporated collagenous matrix: a novel biomaterial for dermal wound healing in rats, *Journal of Biomedical Materials Research Part B: Applied Biomaterials* 73:383-391 (2005).
Tran et al., Matrikines and matricryptins: implications for cutaneous cancers and skin repair, *Journal of Dermatological Science* 40:11-20 (2005).
Heilborn et al., The cathelicidin anti-microbial peptide LL-37 is involved in re-epithelialization of human skin wounds and is lacking in chronic ulcer epithelium, *Journal of Investigative Dermatology* 120:379-389 (2003).
Bessalle et al., Structure-function studies of amphiphilic antibacterial peptides, *J. Med. Chem.* 36:1203-1209 (1993).

(Continued)

*Primary Examiner* — Cecilia J Tsang
*Assistant Examiner* — Satyanarayana Gudibande
(74) *Attorney, Agent, or Firm* — Novak Druce + Quigg LLP

(57) ABSTRACT

The disclosed invention provides tetrapeptides with the amino acid sequence proline-glutamine-glutamate-X (P-Q-E-X), where X can be either lysine (K) or isoleucine (I). These tetrapeptides inhibit ultraviolet light (UV)-induced expression of the pro-inflammatory cytokine interleukin-6 (IL-6) by skin epithelial cells and fibroblasts. Furthermore, the tetrapeptides repress the upregulation of matrix metalloproteinase-1 (MMP-1) by skin fibroblasts induced by either direct exposure to UV rays or treatment with media conditioned by UV-treated keratinocytes. The small size and bio-activity of the tetrapeptides render them suitable for use in therapies directed to inflammatory skin disorders and as active ingredients in skin care products.

20 Claims, 5 Drawing Sheets

OTHER PUBLICATIONS

Oh et al., Design, synthesis and characterization of antimicrobial pseudopeptides corresponding to membrane-active peptide, *J. Peptide Res.* 54:129-136 (1999).

Lee Pha et al. (2004), HB-107, a nonbacteriostatic fragment of the antimicrobial peptide cecropin B, accelerates murine wound repair, *Wound Rep. Reg.* 12:351-358.

Reed Wa et al. (1992), Enhanced in vitro growth of murine fibroblast cells and preimplantation embryos cultured in medium supplemented with an amphipathic peptide, *Mol. Rep. Develop.* 31:106-113.

Andreu D et al. (1985), N-terminal analogues of cecropin A: synthesis, antibacterial activity, and conformational properties, *Biochemistry* 24:1683-1688.

Morgan K et al. (1992), Identification of an immunodominant B-cell epitope in bovine type II collagen and production of antibodies to type II collagen by immunization with a synthetic peptide representing this epitope, *Immunology* 77:609-616.

Degryse B et al. (2005), Domain 2 of the urokinase receptor contains an integrin-interacting epitope with intrinsic signaling activity, *J. Biol. Chem.* 280:24792-24803.

Wu W-J and Raleigh DP (1998), Local control of peptide conformation: stabilization of *cis* proline peptide bonds by aromatic proline interactions, *Biopolymers* 45:381-394.

Kessler E and Yaron A (1973), A novel aminopeptidase from *Clostridium histolyticum*, *Biochem. Biophys. Res. Comm.* 50:405-412.

Wunsch E et al. (1971), Zur spezifitat der kollagenase, *Hoppe-Seyler's Zeitschrift Fuer Physiologische Chemie* 352:1568-1579.

Ye et al. (2002), Distinct molecular mechanism for initiating TRAF6 signalling, *Nature* 418:443-447.

Adhami et al. (2003), Suppression of Ultraviolet B Exposure-Mediated Activation of NF-κB in Normal Human Keratinocytes by Resveratrol, *Neoplasia* 5:74-82.

Tanaka et al. (2005), Prevention of the Ultraviolet B-Mediated Skin Photoaging by a Nuclear Factor κB Inhibitor, Parthenolide, *J. Pharmacol. Experimental Therapeutics* 315:624-630.

Zittermann et al. (2006), Basic Fibroblast Growth Factor (bFGF, FGF-2) Potentiates Leukocyte Recruitment to Inflammation by Enhancing Endothelial Adhesion Molecule Expression, *Am. J. Pathol.* 168 (3):835-846.

Martin et al. (2008), Photoprotective effect of a water-soluble extract of *Rosmarinus officinalis* L. against UV-induced matrix metalloproteinase-1 in human dermal fibroblasts and reconstructed skin, *Eur. J. Dermatol.* 18(2):128-35.

Fagot et al. (2002), Direct role of human dermal fibroblasts and indirect participation of epidermal keratinocytes in MMP-1 production after UV-B irradiation, *Arch. Dermatol. Res.* 293:576-583.

Wang et al. (2006), UVB-irradiated human keratinocytes and interleukin-1α indirectly increase MP kinase/AP-1 activation and MMP-1 production in UVA-irradiated dermal fibroblasts, *Chinese Medical Journal* 119(10):827-831.

Fagot et al. (2004), Matrix Metalloproteinase-1 Production Observed After Solar-Simulated Radiation Exposure is Assumed by Dermal Fibroblasts but Involves a Paracrine Activation Through Epidermal Keratinocytes, *Photochemistry and Photobiology* 79(6):499-505.

Protein Sequence (online database registry) entitled "L-Isoleucinamide, L-prolyl-L-glutaminyl-L-alpha-glutamyl-," Sep. 4, 2008.

* cited by examiner

A

B

A

B

A

B

PROTECTIVE SKIN CARE PEPTIDES

This application claims the benefit of priority to U.S. Provisional Application No. 61/000,815, filed Oct. 29, 2007, which is herein incorporated by reference in its entirety.

FIELD OF THE INVENTION

The invention relates to peptides having biological and therapeutic activity. Particularly, the invention relates to tetrapeptides that inhibit inflammatory processes in skin. Such tetrapeptides exert this effect, in part, by reducing the amount of interleukin (IL)-6 and matrix metalloproteinase (MMP)-1 expressed by skin epithelial and fibroblast cells in response to ultraviolet light (UV) exposure. The invention is further related to methods of using these tetrapeptides to treat various insults affecting the skin and related mucosal surfaces.

BACKGROUND OF THE INVENTION

Exposure to excessive sunlight is an important etiologic factor in the development of acute inflammation, which is characterized by erythema and edema. The long-term consequences of such inflammation include accelerated skin aging and a higher chance of developing skin cancer. Skin inflammation due to acute exposure to UV radiation has been shown to be characterized by the release of various factors including neuropeptides, histamine, prostaglandins, serotonin and oxygen radicals, as well as the upregulation of pro-inflammatory cytokines such as IL-1, IL-6 and tumor necrosis factor alpha (TNF-α). Skin epithelial cells and keratinocytes play an important role in the inflammatory processes observed in skin after UV exposure by producing several of the above factors.

The long term effects of UV-induced inflammation negatively alter skin function. Wound healing processes in skin that has suffered multiple episodes of inflammation are extended in time and can be imperfect (e.g., increased scarring). Furthermore, over-exposed skin is also more prone to wrinkling, dryness, thinning, sagging and greater susceptibility to bruising. The inflammatory processes in skin that lead to these negative effects are complex and likely involve several pathways.

UV light consists of both UVA and UVB rays. UVB is a well known cause of acute inflammation as well as non-melanoma skin cancer. UVB-mediated epidermal inflammation is orchestrated by pro-inflammatory cytokines such as IL-1, IL-6, IL-8 and TNF-α. Since UVB rays penetrate through the epidermis, cytokine induction can occur in keratinocytes, as well as in fibroblasts and endothelial cells that reside in the upper dermis. However, these latter two cell types, which are of mesenchymal origin, can also be induced to an inflammatory state in a manner somewhat indirect from direct UV exposure. Factors (i.e., mediators) expressed by epithelial cells and keratinocytes in response to UV stimulation can signal fibroblasts and endothelial cells to upregulate inflammatory pathways. IL-6 is one such mediator.

The induction of the cytokines such as IL-6 in epithelial cells and fibroblasts has a significant effect on the acceleration of skin photoaging, which manifests itself through wrinkling and sagging, amongst other indications. These effects are primarily mediated by the stimulation of excess MMP-1 expression by fibroblasts in response to IL-6 signaling (Fagot et al. *Arch Dermatol Res.* 293:576, 2002; Fagot et al. *Photochem Photobiol.* 79:499, 2004). MMP-1 overexpression can significantly alter the structural integrity of skin by degrading extracellular matrix (ECM) proteins such as collagen that are comprised in the skin's connective tissue. Furthermore, ECM breakdown enhances the recruitment of immune cells to the site of UV exposure; this heightened cellular activity is a main cause of acute symptoms such as erythema and edema, as well as chronic symptoms such as skin hardening, which results from excess fibrin deposition. Given these far-reaching negative effects on skin physiology in response to UV exposure, IL-6 and MMP-1 represent important molecular targets for controlling skin photoaging.

One means for controlling photoaging is the topical administration of proteins known to inhibit one or more signaling pathways that exhibit altered activity after UV exposure. However, most attempts employing such a strategy have failed to achieve clinically significant results, due in part to difficulties associated with use of entire proteins or large fragments thereof. One problem underlying this failure relates to the inefficient delivery of proteins across the epidermis; most of the applied protein remains distant from the cells that are responsible to initiating photoaging pathways. Other drawbacks relate to the high lability and poor retention of large proteins after administration. Aside from these inherent negative features, the development of these therapies also suffers from the complexity and high costs associated with preparing large proteins. Therefore, less expensive and more effective preparations are presently sought.

Short bio-active peptides represent a potentially useful means for treating and preventing skin photoaging. Besides the immediate benefits of being less expensive and more easily produced and manipulated, short peptides are also better absorbed and retained by skin. Regarding the prevention of photoaging in skin, short peptides (e.g., tetrapeptides) capable of inhibiting skin inflammatory processes are desired.

Although others have previously tested the effects of tetrapeptides on skin, few have been shown to inhibit the inflammatory processes known to be upregulated in skin by UV radiation. For example, Lintner (U.S. Pat. No. 6,974,799) employed certain tetrapeptide-tripeptide mixes to allegedly reverse aging signs in skin; however, this mix was only shown to upregulate ECM production, a process which would not be predicted to prevent the deleterious effects of sunlight. In a similar vein, Sandberg et al. (U.S. Pat. No. 6,962,904) teaches the use of elastin-derived tetrapeptides to restore connective tissue in skin. Particular tetrapeptides are purported by Bissett et al. (U.S. Pat. No. 6,284,802) to be useful for treating wrinkles; the only basis for this utility is the derivation of the peptide from the amino acid sequence of basic fibroblast growth factor (bFGF). As such, these peptides may not be expected to exert anti-inflammatory activity, since bFGF is known to play a positive role in immune cell recruitment (Zittermann and Issekutz *Am J Pathol.* 168:835, 2006). Tetrapeptides described by Dussourd et al. (U.S. Pat. No. 6,211,155) to stimulate epidermal cell proliferation are also not expected to inhibit UV-induced inflammation. On the other hand, the instant invention provides tetrapeptides that downregulate UV-induced inflammation in skin, therefore acting to prevent or treat the main etiology of photoaging.

SUMMARY OF THE INVENTION

The instant invention is directed to an isolated peptide that incorporates as its amino acid sequence proline-glutamine-glutamate-X (P-Q-E-X), where X is either a lysine (K) or isoleucine (I) residue. Therefore, the tetrapeptides SEQ ID NO:14 (PQEK) and SEQ ID NO:15 (PQEI) are examples of isolated peptides provided by the current invention. Though the amino acid sequence of the inventive peptides consist of the above PQEX sequence, the peptide can comprise other features apart from the specific sequence. For example, particular embodiments of the invention are drawn to peptides that are amidated, lipidated or conjugated to a carrier molecule. Other embodiments of the inventive peptide incorporate at least one amino acid residue in the D-enantiomeric form or at least one non-peptide bond present between adjacent amino acid residues.

More specific embodiments of the instant invention include tetrapeptides with amino acid sequences given by SEQ ID NO:1 (PQEK-NH$_2$) and SEQ ID NO:2 (PQEI-NH$_2$). These peptides therefore constitute examples of modified forms of peptides with the PQEX sequence as described above. The tetrapeptides given by SEQ ID NO:1 and SEQ ID NO:2 may have other modifications in addition to amidation at the carboxy terminus.

The instant invention also provides compositions that comprise at least one of the above tetrapeptides having the amino acid sequence PQEX along with a pharmaceutically acceptable carrier. The concentration of the peptide in the composition may be from about 0.1 μg/mL to about 50 μg/mL or from about 0.1 μg/mL to about 20 μg/mL. Preferred embodiments of the inventive composition may be in the form of an aerosol, emulsion, liquid, lotion, cream, paste, ointment, powder, or foam. Still other preferred embodiments of the composition comprise at least one of the tetrapeptides having the amino acid sequence given by SEQ ID NO:1, 2, 14 or 15. The inventive composition can comprise multiple different forms of PQEX tetrapeptides, such as those described herein. Protease inhibitors can be included in all of the above-described compositions.

The instant invention is also drawn to certain methods that employ the abovementioned inventive peptides and pharmaceutical compositions. In particular, the invention embraces a method for treating inflammation in a mammal that includes the step of administering a therapeutically effective amount of the inventive composition/peptide to a site of inflammation for an effective amount of time. Inflammation that accompanies or results from abrasions, blisters, burns, lacerations, ulcers, bruises, rashes and scars is amenable to being treated by the inventive method. Preferred embodiments of the inventive method employ at least one of the above peptides, such as SEQ ID NO:1 or SEQ ID NO:2, at a concentration ranging from about 0.1 μg/mL to about 50 μg/mL or from about 0.1 μg/mL to about 20 μg/mL.

Certain embodiments of the inventive method are directed to treating inflammation that occurs in the skin or associated tissue such as within the oral cavity. Still another embodiment of the inventive method is drawn to treating skin inflammation that occurs as a result of exposure to ultraviolet (UV) radiation (e.g., sunburn). Tetrapeptides given by SEQ ID NO:1 or SEQ ID NO:2, for example, may be employed in this preferred embodiment.

The instant invention is also drawn to a method of inhibiting the expression of IL-6 and/or MMP-1 by a cell. This method comprises the step of exposing a cell to a peptide as described in the above text. Such exposure to the peptide results in reduced expression by the cell of either or both these inflammatory mediators. The exposing step can be performed by contacting the cell with the peptide, which can be accomplished by simple incubation means. The peptides that can be employed in this method, either individually or in combination, are preferably SEQ ID NO:14, SEQ ID NO:1, SEQ ID NO:15 and SEQ ID NO:2. In a particular embodiment of this method, the cellular expression of IL-6 or MMP-1 is a result of exposure of the cell to ultraviolet radiation, such as UVA and/or UVB rays. However, the method is also applicable to controlling the cellular expression of IL-6 and/or MMP-1 that occurs as a result of any other inflammatory-related event such as trauma or burns. Preferred embodiments of this method are directed to cells that are either derived from the skin (e.g., primary or immortalized cells, in vitro or ex vivo) or otherwise present in the skin (i.e., in vivo); such cells can be skin epithelial cells, keratinocytes, and skin fibroblasts. Other embodiments of the method can be employed using any type of epithelial or fibroblast cell.

DETAILED DESCRIPTION OF THE INVENTION

Figure 1:
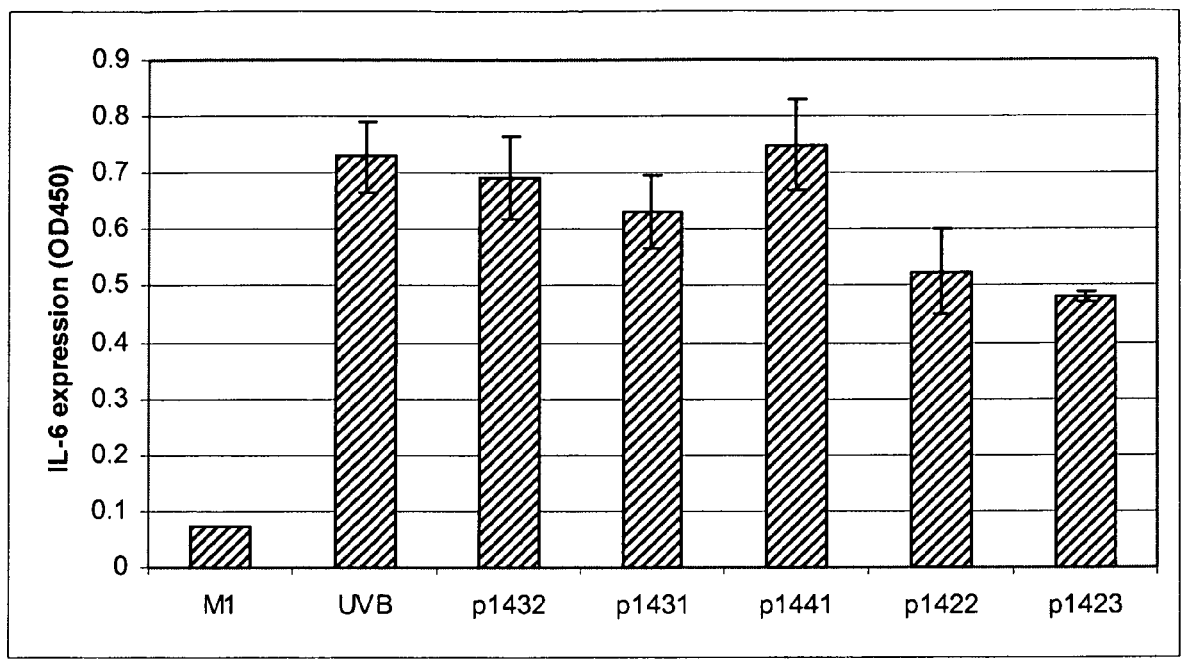
FIG. 1 shows the effect of certain tetrapeptides (40 μg/mL) on IL-6 expression by human epithelial cells 24 hours post UVB exposure. "M1" denotes a non-irradiated control cell culture (no peptide treatment) and thus shows the basal IL-6 expression level of skin epithelial cells. "UVB" denotes an irradiated control cell culture (no peptide treatment) and thus shows the level of IL-6 induced in the epithelial cells upon UVB exposure. Refer to Example 3.

The peptides of the present invention are tetrapeptides with the amino acid sequence proline-glutamine-glutamate-X (P-Q-E-X), where X can be either lysine (K) or isoleucine (I). Therefore, tetrapeptides PQEK (SEQ ID NO:14) and PQEI (SEQ ID NO:15) are provided by the instant invention. Non-limiting examples of SEQ ID NO:14 and SEQ ID NO:15 are SEQ ID NO:1 and SEQ ID NO:2, respectively; these latter tetrapeptides are amidated at their respective carboxy termini. Just for reference purpose, the three-letter codes of the amino acid residues in the inventive peptides are Pro (proline, P), Gln (glutamine, Q), Glu (glutamate or glutamic acid, E), Lys (lysine, K) and Ile (isoleucine, I).

A biological activity elicited by the above tetrapeptides is the inhibition of skin inflammation at the site of UV exposure. This activity is achieved in part via the peptides' negative effect on secretion of IL-6 by skin epithelial cells and fibroblasts (refer to Examples). IL-6 secretion in this environment is due to the effects of UV radiation on these cells. The inhibitory activity of the above tetrapeptides on inflammation is further due in part to their negative effect on MMP-1 expression in fibroblasts.

Skilled artisans would recognize that, given the ability of the inventive tetrapeptides PQEK (SEQ ID NO:14) and PQEI (SEQ ID NO:15) to inhibit IL-6 production, these peptides will additionally be useful for treating forms of skin damage resulting from insults other than UV exposure. Furthermore, it would be acknowledged that the inventive peptides will be useful for treating wounds to mucosal tissue. IL-6 is released by keratinocytes and fibroblasts at wound sites and signals for immune cell infiltration, a process which can actually aggravate healing and cause scarring. Control of IL-6 expression under such circumstances by the application of the inventive peptides will ameliorate these negative wound healing processes. These biological activities are listed to provide guidance on how the inventive peptides may be used therapeutically; however, the instant invention is not limited in any fashion by these particular modes of peptide function.

Peptides

Each of the inventive tetrapeptides [e.g., PQEK (SEQ ID NO:14) and PQEI (SEQ ID NO:15)] can comprise L- or D-amino acid enantiomers, either containing residues of one enantiomeric form or a combination of both forms. The peptides may be further augmented or modified as described in the following non-limiting examples, just so long as their primary amino acid sequences are unaltered; in this manner, the peptides consist of a certain amino acid sequence, but may comprise certain modifications. The carboxy-terminus of the peptides can be acidic (—COOH) or be amidated (e.g., —CONH$_2$, —CONHR, or —CONR$_2$). Amidation of the carboxy-terminus may render the inventive peptides less susceptible to protease degradation and increase their solubility compared to their free acid forms, therefore providing heightened therapeutic potency. Examples of peptides of the instant invention that are carboxy-amidated are SEQ ID NO:1 and SEQ ID NO:2. The peptides may also be lipidated, which may provide for enhanced skin penetration. One or more of the molecular bonds that link the amino acids of each peptide may be a non-peptide bond. Such non-peptide bonds include, but are not limited to, imido, ester hydrazine, semicarbazoide and azo bonds. Other examples of peptides according to the above description are those that incorporate SEQ ID NO:1 and SEQ ID NO:2 with further modifications (note that both SEQ ID NO:1 and 2 are already carboxy-amidated).

A variety of modifications can be made to the inventive tetrapeptides as long as their primary amino acid sequences are retained. Some modifications may be used to increase the potency of the peptide, while other modifications may facilitate peptide handling. Peptide functional groups that may typically be modified include hydroxyl, amino, guanidinium, carboxyl, and amide groups. Typical, non-limiting reactions of these groups include the following: acetylation of hydroxyl groups by alkyl halides; esterification, amidation or hydrogenization (i.e., reduction to alcohol) of carboxyl groups; deamidation, acylation, alkylation, arylation of amino groups (e.g., primary amino group of the peptide or the amino group of lysine residues).

Peptides may be conjugated to soluble or insoluble carrier molecules to modify their solubility properties as needed and to increase the local concentrations of peptides in targeted tissues. Examples of soluble carrier molecules include polymers of polyethyleneglycol (PEG) and polyvinylpyrrolidone; examples of insoluble polymers include silicates, polystyrene, and cellulose. Peptides may also be micro-encapsulated to enhance their stability during and after therapeutic application; typically, polyester and PEG microspheres are used to encapsulate and stabilize the peptides.

Various methods of preparing microspheres for peptide encapsulation may be employed depending upon the hydrophilic or hydrophobic nature of the peptide composition to be encapsulated. Examples of protocols for such methods are found in Wang et al. (*J. Control. Release* 17:23, 1991) and U.S. Pat. No. 4,324,683, both of which are herein incorporated by reference in their entirety. In vitro peptide release studies may be performed to determine the relative availability of the peptide after incorporation into a microsphere. Microspheres (200 mg) are suspended in 2.5 mL phosphate-buffered saline (PBS, pH 7.2) and agitated at 37° C. and 100 rpm in an environmental incubator shaker (G-24, New Brunswick Scientific Co., Edison, N.J.). At specific sampling times (each day for the first 4 days and every other day thereafter) the buffer solution is completely removed and replaced with fresh PBS. The peptide content of the PBS is measured using the Bradford method or other suitable quantitative assay typically used for protein analysis.

The following procedures and parameters are provided for guidance purposes only and are all well known to those skilled in the art. All the disclosed peptides may be synthesized using standard Fmoc (9-fluorenylmethoxycarbonyl) solid-phase chemistry on an Advanced ChemTech Apex 396 Multiple Peptide Synthesizer. The Apex 396 is equipped with a 40-well reaction block for the production of up to 40 peptides simultaneously at a scale of 0.15 mmol. The peptides can be prepared as either amidated or free acid sequences using standard amino acids. The resin is first washed and pre-swelled with N,N-dimethyl formamide (DMF). The swelling time is one hour for Rink amide resins. The Fmoc protecting group is removed with 25% piperidine in DMF for 25 minutes, after which the piperidine is completely washed from the resin. To control racemization processes, the Fmoc amino acid monomers are pre-activated in an equimolar solution of 1-hydroxy-benzotriazole (HOBt) or 1-hydroxy-7-azabenzotriazole (HOAt) in 0.5 M DMF. The amide couplings are carried out using O-(7-azabenzotriazol-1-yl)-1,1,3,3-tetramethyluronium hexafluorophosphate (HATU) PyBop® or 2-(1H-benzotriazol-1-yl-)-1,1,3,3-tetrameth-yluronium hexafluorophosphate (HBTU) as an activation agent and 2.5-5.0 fold molar excess of amino acid under basic conditions using a hindered base (diisopropylethylamine). The coupling times are 1-1.5 hours followed by a wash and re-coupling to accomplish a double or triple couple before deprotection and continuation of the growing peptide chain. Coupling efficiency is monitored using the standard Kaiser test. Once peptide synthesis is completed on the resin, the final Fmoc group is removed as above and the sequences are left as the free base form.

Cleavage of the acid-labile linkage of the peptide to the resin is accomplished using 95% trifluoroacetic acid (TFA) and water with the appropriate scavengers added. After cleavage is allowed to proceed for about 30 minutes to one hour, the released peptides are immediately removed from the cleavage block and transferred to tubes for the removal of the TFA under reduced pressure. The peptides are then ready for purification and analysis via high performance liquid chromatography (HPLC) using a reverse phase C18 column and mass spectrometry. Primary sequence confirmation and preparative purification are accomplished using an LC/MS/MS system (ABI API2000).

General to the above protocol, the peptides may be produced using any method known to those skilled in the art such as those disclosed in Merrifield (*J Am Chem Soc.* 85:2149, 1963); Carpino et al. (*J Org Chem.* 51:3732, 1986); Merrifield et al. (*Anal Chem.* 38:1905, 1966); or Kent et al. [*High Yield Chemical Synthesis Of Biologically Active Peptides On An Automated Peptide Synthesizer Of Novel Design*, IN: PEPTIDES 1984 (Ragnarsson, ed.) Almqvist and Wiksell Int., Stockholm (Sweden), pp. 185-188], all of which are herein incorporated by reference in their entirety. Preferably, the peptides will be produced by a machine capable of sequential addition of amino acids to a growing peptide chain. However, the peptides may also be manufactured using standard solution phase methodology, which can be amenable to large-scale production efforts.

The instant invention can comprise one or more protease inhibitors. A protease inhibitor can be selected to specifically target proteases that would be expected to degrade the selected bioactive peptide; such a selection would be determined based on the length and/or sequence of the bioactive peptide. However, protease inhibitors need not necessarily be selected in any specific manner; for example, a protease inhibitor cocktail, which contains two or more inhibitors, can be employed in the instant invention. With certain embodiments of the invention, the protease inhibitor is not one that is specific to inhibiting a virus. The following types of protease inhibitors can be incorporated in the invention: serine protease inhibitors, cysteine protease inhibitors, aspartate protease inhibitors, metalloproteinase inhibitors, thiol protease inhibitors and threonine protease inhibitors Protease inhibitors are well known in the art. Non-limiting examples of protease inhibitors that can be incorporated in the present invention include acetyl-pepstatin, AEBSF (4-[2-Aminoethyl] benzenesulfonyl fluoride) hydrochloride, ALLM (N-Acetyl-Leu-Leu-Met), ALLN (N-Acetyl-Leu-Leu-Nle-CHO), amastatin (*Streptomyces* sp.), ε-amino-n-caproic acid, aminopeptidase N inhibitor, $\alpha_1$-antichymotrypsin, antipain (hydrochloride or dihydrochloride), α2-antiplasmin, antithrombin III, α1-antitrypsin, p-APMSF hydrochloride, aprotinin (e.g., from bovine lung), ATBI (an 11-residue peptide), benzamidine hydrochloride, bestatin, bestatin methyl ester, calpastatin, calpeptin, carboxypeptidase inhibitor, caspase inhibitor, cathepsin B inhibitor II, cathepsin G inhibitor I, cathepsin inhibitor II, cathepsin inhibitor III, cathepsin inhibitor I, cathepsin K inhibitor I, cathepsin K inhibitor II, cathepsin K inhibitor III, cathepsin L inhibitor I, cathepsin L inhibitor II, cathepsin L inhibitor IV, cathepsin L inhibitor V, cathepsin L inhibitor VI, cathepsin S inhibitor, cathepsin/subtilisin inhibitor, chymostatin, chymotrypsin inhibitor I, cystatin, 1,5-dansyl-glu-gly-arg chloromethyl ketone dihydrochloride, 3,4-dichloroisocoumarin, diisopropylfluorophosphate, dipeptidylpeptidase II inhibitor, dipeptidylpeptidase IV inhibitor I, dipeptidylpeptidase IV inhibitor II, E-64 protease inhibitor, ecotin, EDTA disodium salt dihydrate, EDTA tetrasodium salt, EGTA, elastase inhibitor I, elastase inhibitor II, elastase inhibitor III, elastatinal, 6-amidino-2-naphthyl-4-guanidinobenzoate dimethanesulfonate, glu-gly-arg-chloromethyl ketone, 2-guanidinoethylmercaptosuccinic acid, hexadecylsulfonyl fluoride, α-iodoacetamide, kininogen, leuhistin, leupeptin hemisulfate, $\alpha_2$-macroglobulin, DL-2-mercaptomethyl-3-guanidinoethylthiopropanoic acid, pepstatin A, phenylmethylsulfonyl fluoride, phosphoramidon Disodium Salt, PPack II trifluoroacetate salt, PPack dihydrochloride, prolyl endopeptidase inhibitor II, Na-tosyl-lys chloromethyl ketone hydrochloride, Na-tosyl-phe chloromethyl ketone, tripeptidylpeptidase II inhibitor, trypsin inhibitor (from corn or soybean), D-val-phe-lys chloromethyl ketone dihydrochloride, 1,3-di-(N-carboxybenzoyl-L-leucyl-L-leucyl)amino acetone, o-phenanthroline, ursolic acid (e.g., Rosemary extract), tranexamic acid (4-[aminomethyl]cyclohexane-1-carboxylic acid) (clinically marketed as Cyklokapron in the U.S. and as Transamin in Asia), Fmoc-Lys (Boc), Fmoc-Arg(Pmc), benzoyl-Arg-nitroanilide, benzoyl-Arg-naphthylamide, and α-2-macroglobuline.

The protease inhibitor used in the invention may be a peptide or protein, such as an enzyme. Non-limiting examples of such inhibitors are the serpins, which include alpha-1-antitrypsin, complement 1-inhibitor, antithrombin, alpha-1-antichymotrypsin, plasminogen activator inhibitor 1, and neuroserpin.

Components that are typically incorporated into skin care preparations are well known in the art. Beside the bioactive peptide component, the instant invention can contain other active agents such as niacinamide, phytantriol, farnesol, bisabolol and salicylic acid. It is expected that certain additional active agents will act synergistically with the bioactive peptide component, or will enhance the shelf-life of the formulation.

Where the composition is to be in contact with animal or human skin, additional components should be chosen that are suitable for application to keratinous tissue (i.e., stabile, low toxicity, hypoallergenic). The CTFA Cosmetic Ingredient Handbook, Second Edition (1992), which is herein incorporated by reference in its entirety, describes a wide variety of non-limiting cosmetic and pharmaceutical ingredients commonly used in the skin care industry that are suitable for use in the compositions of the present invention. Examples of these ingredient include: abrasives, absorbents, aesthetic components such as fragrances, pigments, colorings/colorants, essential oils, skin sensates, astringents, etc. (e.g., clove oil, menthol, camphor, eucalyptus oil, eugenol, menthyl lactate, witch hazel distillate), anti-acne agents (e.g., resorcinol, sulfur, salicylic acid, benzoyl peroxide, erythromycin, zinc), anti-caking agents, antifoaming agents, antimicrobial agents (e.g., iodopropyl butylcarbamate), antioxidants, binders, biological additives, buffering agents, bulking agents, chelating agents, chemical additives, denaturants, external analgesics, polymers (e.g., copolymer of eicosene and vinyl pyrrolidone), opacifying agents, pH adjusters, propellants, reducing agents, sequestrants, skin bleaching and lightening agents (e.g., hydroquinone, kojic acid, ascorbic acid, magnesium ascorbyl phosphate, ascorbyl glucosamine), skin-conditioning agents (e.g., humectants, including miscellaneous and occlusive), skin soothing and/or healing agents (e.g., panthenol and derivatives [e.g., ethyl panthenol], aloe vera, pantothenic acid and its derivatives, allantoin, bisabolol, dipotassium glycyrrhizinate), thickeners, particulate materials, structuring agents and vitamins. Many of these agents are described in detail in U.S. Pat. No. 6,492,326, which is herein incorporated by reference in its entirety, specifically with respect to the various ingredient descriptions.

The compositions of the present invention may contain a particulate material, preferably a metallic oxide. These particulates can be coated or uncoated, charged or uncharged. Non-limiting examples of particulate materials useful for preparing the instant invention include bismuth oxychloride, iron oxide, mica, mica treated with barium sulfate and $TiO_2$, silica, nylon, polyethylene, talc, styrene, polyproylene, ethylene/acrylic acid copolymer, sericite, aluminum oxide, silicone resin, barium sulfate, calcium carbonate, cellulose acetate, titanium dioxide, polymethyl methacrylate, and mixtures thereof. Inorganic particulate materials such as $TiO_2$, ZnO (zinc oxide), or $ZrO_2$ are commercially available from a number of sources. Preferably, particulate materials are present in the composition at levels of from 0.01% to 2% by weight, more preferably from 0.05% to 1.5% by weight, or still more preferably from 0.1% to 1% by weight (all measures approximate).

The compositions of the present invention may contain a conditioning agent selected from humectants, moisturizers, or skin conditioners. A variety of these materials can be employed and each can be present at a level of from 0.01% to 20%, more preferably from 0.1% to 10%, and still more preferably from 0.5% to 7% by weight of the composition (all measures approximate). These materials include, but are not limited to, guanidine; urea; glycolic acid and glycolate salts (e.g. ammonium and quaternary alkyl ammonium); salicylic acid; lactic acid and lactate salts (e.g., ammonium and quaternary alkyl ammonium); aloe vera in any of its variety of forms (e.g., aloe vera gel); polyhydroxy alcohols such as sorbitol, mannitol, xylitol, erythritol, glycerol, hexanetriol, butanetriol, propylene glycol, butylene glycol and hexylene glycol; polyethylene glycols; sugars (e.g., melibiose) and starches; sugar and starch derivatives (e.g., alkoxylated glucose, fructose, glucosamine); hyaluronic acid; lactamide monoethanolamine; acetamide monoethanolamine; panthenol; allantoin; petroleum jelly; and mixtures thereof.

The compositions of the present invention can contain a structuring agent, which is preferred for preparing a oil-in-water emulsion. Without being limited by any theory, it is believed that the structuring agent assists in providing rheological characteristics to the composition which contribute to the stability of the composition. For example, the structuring agent tends to assist in the formation of liquid crystalline gel network structures. The structuring agent may also function as an emulsifier or surfactant. Preferred compositions of this invention contain from 0.1% to 20%, more preferably from 0.1% to 10%, still more preferably from 0.5% to 9%, of one or more structuring agents by weight of the composition (all measures approximate).

Preferred structuring agents for incorporation in the present invention are selected from stearic acid, palmitic acid, stearyl alcohol, cetyl alcohol, behenyl alcohol, the polyethylene glycol ether of stearyl alcohol having an average of about 1 to about 5 ethylene oxide units, the polyethylene glycol ether of cetyl alcohol having an average of about 1 to about 5 ethylene oxide units, and mixtures thereof. More preferred structuring agents of the present invention are selected from stearyl alcohol, cetyl alcohol, behenyl alcohol, the polyethylene glycol ether of stearyl alcohol having an average of about 2 ethylene oxide units (steareth-2), the polyethylene glycol ether of cetyl alcohol having an average of about 2 ethylene oxide units, and mixtures thereof.

Methods of Use

Additional embodiments of the current invention are directed towards methods of using the above-described peptides, such as in formulations or as therapeutic agents. These methods may involve the use of a single peptide, or multiple peptides in combination.

The peptides of the current invention may be used for treating and preventing damage to skin by over-exposure to UV rays. Also, the peptides may be used for treating wounds of the skin (epidermis, dermis and hypodermis) and associated mucosal tissues. The salutary effects of the inventive peptides toward these conditions is related in part to their anti-inflammatory properties. As used herein, the term "associated mucosal tissues" relates to any tissue organized in a manner similar to the skin and contains epithelial cells. Examples of such tissues are oral, nasopharyngeal, aural and urogenital surfaces, as well as the palpebral conjunctiva of the eye. Other examples of associated mucosal tissues include the entire lining (i.e., lumen) of the alimentary canal, including the esophagus, stomach, small intestine, large intestine (colon), and rectum. These latter examples can sustain wounds/lesions much like those that can affect the skin, and as such can be targeted with the present invention. Examples of wounds/lesions/injuries that can affect these tissues and are amenable to treatment with the inventive peptides are abrasions, blisters, burns, lacerations, punctures, ulcers, bruises, rashes and scars. Post-surgical tissue trauma can also be treated with the peptides. Though inflammation aids in warding off infection at injury sites, the provision of good antiseptic practices negates any drawbacks that may be associated with blocking inflammation using the inventive peptides.

The inventive peptides may also be used to prevent or reverse the effects of aging on all of the abovementioned tissues. In a related manner, the peptides could be applied to tissue that has been damaged by exposure to various external agents such as sunlight. Examples of skin debilitation related to aging and exposure are skin wrinkling, dryness, thinning, sagging and greater susceptibility to bruising. The invention can also be used as a cosmetic in these regards to render a more youthful appearance and texture to skin, and to provide better function.

Other tissue problems that are effectively treated using the peptides of the present invention are related to allergy or autoimmunity, both of which have an inflammatory component. Such maladies include dermatitis, psoriasis, scleroderma, pemphigus and inflammatory bowel disease.

The compositions used to deliver the peptides in the above therapeutic method can be in the form of an aerosol, emulsion, liquid, lotion, cream, paste, ointment, powder, foam, or other pharmaceutically acceptable formulation. Furthermore, the peptides can be delivered using less involved formulations such as deionized/distilled water, PBS or standard medical saline solutions. Generally, a pharmaceutically acceptable formulation would include any carrier suitable for use on human skin or mucosal surface. Such pharmaceutically acceptable carriers include ethanol, dimethyl sulfoxide, glycerol, silica, alumina, starch, and equivalent carriers and diluents. The formulation may optionally have cosmetic appeal, and/or contain other agents such as retinoids or other peptides that can act as adjuvants for the therapeutic action of the inventive peptides. Antibiotics can also be added to the formulation in order to ward off infection, thereby permitting maximal healing processes to occur. The concentration of the peptide in the composition can be about 0.1 μg/mL to about 50 μg/mL or about 0.1 μg/mL to about 20 μg/mL; however, the ultimate concentration employed may vary outside these ranges, depending on the nature of the wound/tissue condition, the bio-activity of the inventive peptide and the use of any adjuvant or technique to obtain enhanced composition absorption. Such determinations are well within the normal skill in the art.

The administration of the inventive peptides and associated compositions may be made to humans and animals, including all mammals (e.g., pigs, cows, horses, sheep, goats, mice, rats, cats, dogs, ferrets). Application may also be made in combination with typical and/or experimental materials such as tissue grafts, tissue culture products, oxygen and dressings. In general, the composition can be administered topically, orally, transdermally, systemically, or by any other method known to those of skill in the art to be useful to deliver the inventive peptides to the inflammatory site. Compositions may also be applied in an in vitro or ex vivo manner, either to cells or patient grafts growing in culture, for example.

Due to their small size, the peptides are expected to be able to gain by themselves some level of permeability through the skin; however, certain techniques may be used to amplify this movement. For example, lipophilic (non-polar) groups can be added to the peptides, or the peptides can be delivered to the skin in a lipophilic excipient, in order to enhance peptide accessibility to the stratum corneum to allow translocation to the lower epidermal layers. In this manner such lipophilic modifications may be considered as having a pro-drug effect. Permeation enhancers such as known solvents and surfactants may be used in the excipient to allow better peptide absorption. Special techniques that are anticipated to be useful in enhancing peptide access to the targeted tissue/injury include iontophoresis, electrophoresis and ultrasound. An iontophoretic device consists of two electrodes immersed in an electrolyte solution and placed on the skin. When an electric current is applied across the electrodes, an electric field is created across the stratum corneum that drives the delivery of the peptides. Electroporation involves the application of high-voltage electric pulses to increase the permeation through lipid bilayers. This differs from iontophoresis in the duration and intensity of the application of electrical current (iontophoresis uses a relatively constant low-voltage electric field). The high-voltage electric pulse of electroporation is believed to induce a reversible formation of hydrophilic pores in the lipid lamellae membranes that can provide a high degree of permeation enhancement. Ultrasound applies sound waves having a frequency greater than 16 kHz to the skin, which causes compression and expansion of the tissue through which the sound waves travel. The resulting pressure variations cause a number of processes (e.g., cavitation, mixing, increase in temperature) that may enhance permeation of the peptides.

Additional features, modes of production and use of the inventive peptides are described, for example, in U.S. Pat. Nos. 6,974,799 and 5,492,894. Both these patents are incorporated herein by reference in their entirety.

The following examples are included to demonstrate certain preferred embodiments of the invention.

EXAMPLES

The aim in developing the instant invention was to identify peptides of less than 500 Daltons that have the capacity to down-regulate inflammatory processes such as those elicited by UV radiation. The small molecular weight of such identified peptides would ensure their ability to penetrate across the upper layers of the skin. The following insights inferred from the prior art partly guided the development of the instant invention.

1. UV radiation causes inflammation that leads to the production of cytokines and the subsequent induction of elements that contribute to skin photoaging. Certain hallmarks of this latter process are wrinkling due to collagen breakdown, skin thickening due to excessive keratinocyte proliferation and fibrin deposition, and hyper-pigmentation due to melanin over-production. Factors that initiate UV-induced inflammation are cytokines such as IL-1, IL-6, IL-8 and TNF-α.

2. Certain peptide sequences have been identified that can inhibit the binding of TRAF6 (TNF receptor-associated factor-6) to a wide range of immuno-regulatory proteins including human CD40, Trance and IRAK (IL-1 receptor-associated kinase). These TRAF6-related binding events relay stimuli from TNF, IL-1 and toll-like receptor family proteins to NF-$_K$B, which is a central regulator of cellular immune responses. Peptides that inhibit these TRAF6 binding events have the general formula Pro-X-Glu-X-X-(aromatic/acidic amino acid) [PXQXX-(aromatic/acidic)] (SEQ ID NO:16) and are located in several TRAF6-interacting proteins.

3. Peptides containing the sequence PXQXX-(aromatic/acidic) (SEQ ID NO:16) cannot be used to combat photoaging for several reasons. For one, this peptide must be incorporated within a fusion protein to exert its inhibitory effects; such large proteins would not efficiently dissolve across the upper skin layers to access the inflammatory reaction site. Also, on a practical level, fusion peptides having the inhibitory peptide sequence would be too large and expensive for inclusion in a topical product.

4. The NF-κB signaling pathway is the predominant pathway directly involved in the regulation of pro-inflammatory cytokines and stress response. It has been shown that exposure of skin cells to various NF-κB activators, including TNF-α, lipopolysaccharides and UV light leads to phosphorylation and degradation of the inhibitory protein IkappaB. Liberated NF-κB is subsequently translocated into the nucleus where it modulates the expression of cytokines.

5. Various types of collagen contribute to the extracellular matrices comprised in different connective tissues of the body. These different collagens are degraded by specific MMPs produced by fibroblasts, other connective tissue cells, and inflammatory cells that are induced by pro-inflammatory cytokines such as IL-1 and TNF. It is evident that IL-1, IL-6, TNF-α, and interferons (IFN-α and IFN-γ) which are released in response to inflammatory stimuli are potent inducers of MMPs. Although the regulation of MMP secretion is dependent on the cell type and stimulus, it has been shown that the transcriptional factor AP-1 is directly linked to upregulation of MMP-1 in fibroblasts. It has also been shown in vitro and in vivo that AP-1 activity and consequent MMP expression in skin is induced by UV radiation.

Based on these insights, it was posited that, although the PXQXX-(aromatic/acidic) (SEQ ID NO:16) peptide has only been shown to inhibit non-UV-induced inflammatory processes, a related sequence might be devised that is capable of inhibiting UV-induced inflammation while not requiring incorporation within in a fusion protein (i.e., the peptide would be a short peptide). Examples 1-5 below relate to this topic. Example 6 relates to the general use of protease inhibitors in compositions comprising bioactive peptides.

Example 1

Design and Synthesis of Peptides that are Related to the PXQXX-(Aromatic/Acidic) (SEQ ID NO:16) Peptide The rational for designing the inventive peptides involved the following parameters:
1. Peptides are only four amino acids in length (i.e., tetrapeptides less than 500 Daltons).
2. Sequences are selected from the conserved binding domain [PXQXX-(aromatic/acidic)] (SEQ ID NO:16) of TRAF6-binding proteins.
3. Tetrapeptide sequences conserve the proline in position 1 and the glutamate in position 3 of PXQXX-(aromatic/acidic) (SEQ ID NO:16).
4. Positions 2 and 4 are assigned amino acid residues that exist at these sites in naturally occurring forms of PXQXX-(aromatic/acidic) (SEQ ID NO:16):
    a. Position 2: Q, T, L, G, E, V or P.
    b. Position 4: I, M, D, V, N, S or T.
5. To create additional variation, a positively charged residue was also used in position 4; such an amino acid placement has been avoided in nature.

Peptide synthesis: All peptides were synthesized using standard Fmoc chemistry on an Advanced ChemTech (Louisville, Ky.) Apex 396 Multiple Peptide Synthesizer. The Rink amide resin was first washed and pre-swelled with DMF. The Fmoc-protecting group was removed with 25% piperidine in DMF, after which the resin was washed to remove traces of piperidine. The Fmoc amino acid monomers were pre-activated in an equimolar (0.5 M) solution of HOAt or HOBt in DMF. The amide couplings were carried out using HATU, PyBop or HBTU and 2.5- to 5-fold molar excess of amino acid under basic conditions using a hindered base (diisopropylethylamine). Coupling efficiency was monitored using the standard Kaiser test.

Cleavage of the peptide from the acid labile linker was accomplished using 95% trifluoroacetic acid and water with the appropriate scavengers added. After removal from the cleavage block, these peptides were purified and analyzed via HPLC using a reverse phase C-18 column and mass spectrometry. Primary sequence confirmation and preparative purification was accomplished using an LC/MS/MS system (ABI API2000). Sequences of the prepared peptides are provided in Table 1.

TABLE 1

Peptide Sequences

| HBX# | P# | SEQ ID NO | Sequence (N→C terminus) |
|---|---|---|---|
| 20 | 1422 | 1 | PQEK-NH$_2$ |
| 21 | 1423 | 2 | PQEI-NH$_2$ |
| 22 | 1424 | 3 | PQEM-NH$_2$ |
| 23 | 1425 | 4 | PTED-NH$_2$ |
| 24 | 1426 | 5 | PGED-NH$_2$ |
| 25 | 1427 | 6 | PLEV-NH$_2$ |
| 26 | 1428 | 7 | PQEN-NH$_2$ |
| 27 | 1429 | 8 | PVES-NH$_2$ |
| 28 | 1430 | 9 | PEES-NH$_2$ |
| 29 | 1431 | 10 | PVET-NH$_2$ |
| 30 | 1432 | 11 | PEET-NH$_2$ |
| 31 | 1433 | 12 | PPEN-NH$_2$ |
| 32 | 1434 | 13 | PTEN-NH$_2$ |

Example 2

Cell Cultures and Detection of IL-6 and MMP-1

Human skin epithelial cells (ATCC CRL-2592), keratinocytes (ATCC CRL-2404) and skin fibroblasts (ATCC CRL-7481) were employed in the study. Cells were seeded into 6-well plates and allowed to grow to >95% confluence in Dulbecco's modified Eagle's medium (DMEM; 4 mM L-glutamine, 4.5 g/L glucose) adjusted to contain 1.5 g/L sodium bicarbonate and supplemented with 10% fetal bovine serum (FBS). For keratinocytes, cells were grown in keratinocyte growth media (without serum) supplemented with 5 ng/mL human recombinant epithelial growth factor (EGF; Invitrogen, Grand Island, N.Y.). After the cell monolayer reached >95% confluence, the cells were serum-starved or EGF-starved for 24 hours in complete medium without serum. UVA or UVB was generated using a UVLMS lamp (4-W model, 3UV assembly; Upland, Calif.) with the irradiation wavelength set at 365 or 302 nm, respectively. The UV lamp was placed 15 cm above the tissue culture plate. Before UV treatment, the tissue culture media was replaced with PBS, after which the cells were placed under the UVB lamp (450 µW/cm$^2$, measured using a radiometer) for 35 seconds (epithelial cells and fibroblasts) or 25 seconds (keratinocytes). UVA treatment was conducted (500 µW/cm$^2$) for 30 seconds with fibroblasts. After UV treatment, PBS was immediately replaced with complete medium (without serum or EGF) containing either no peptide or peptide at a specified concentration, and the plates were incubated at 37° C., 5% CO$_2$ for 15-24 hours. The cell media was then collected and spun down at 15000 rpm for 2 minutes to remove cell debris. IL-6 and MMP-1 levels in the media were measured, respectively, using human IL-6 (DIACLONE, Stamford, Conn.) and MMP-1 (Calbiochem, San Diego, Calif.) ELISA kits according to manufacturers' instructions. These measurements served as indicators of cell inflammatory activity in response to UV exposure.

Example 3

Screening Peptides for Anti-inflammatory Activity: Inhibition of UV-induced IL-6 Expression in Human Skin Epithelial Cells As shown in FIG. 1, human epithelial cells upregulate IL-6 expression in response to UVB irradiation. All the tetrapeptides listed in Table I were subjected to a screening test at 40 µg/mL for potential down-regulation of this response (data not shown). Those peptides that down-regulated IL-6 expression in a first experiment were retested in a second experiment, the results of which are shown in FIG. 1.

Figure 2:
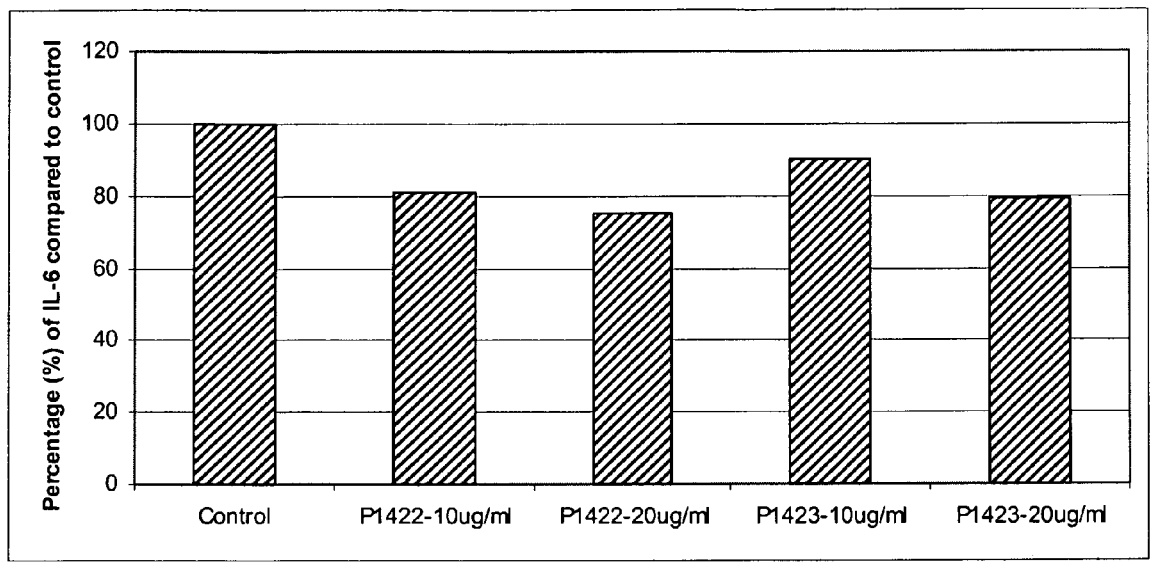
FIG. 2 shows the effect of tetrapeptides P1422 (SEQ ID NO:1) and P1423 (SEQ ID NO:2) at two different concentrations (10 and 20 μg/mL) on IL-6 induction in skin epithelial cells treated with UVB. "Control" denotes cells that were UVB-irradiated, but did not receive peptide. Refer to Example 3.

Both tetrapeptides P1422 (SEQ ID NO:1) and P1423 (SEQ ID NO:2) at 40 µg/mL showed reproducible repression of UVB-induced IL-6 expression in skin epithelial cells. As shown in FIG. 2, such down-regulation was concentration-dependent for both these peptides. P1422 (SEQ ID NO:1) reduced IL-6 levels by 19% and 25% at 10 and 20 µg/mL, respectively; and P1423 (SEQ ID NO:2) reduced IL-6 levels by 10% and 20% at 10 and 20 µg/mL, respectively. The fact that the inhibitory effect towards IL-6 expression was not observed when cells were treated with other tetrapeptides aside from P1422 (SEQ ID NO:1) and P1423 (SEQ ID NO:2) suggests that the novel anti-inflammatory activity lies in specific sequences such SEQ ID NO:14 and SEQ ID NO:15.

Example 4

Figure 3:
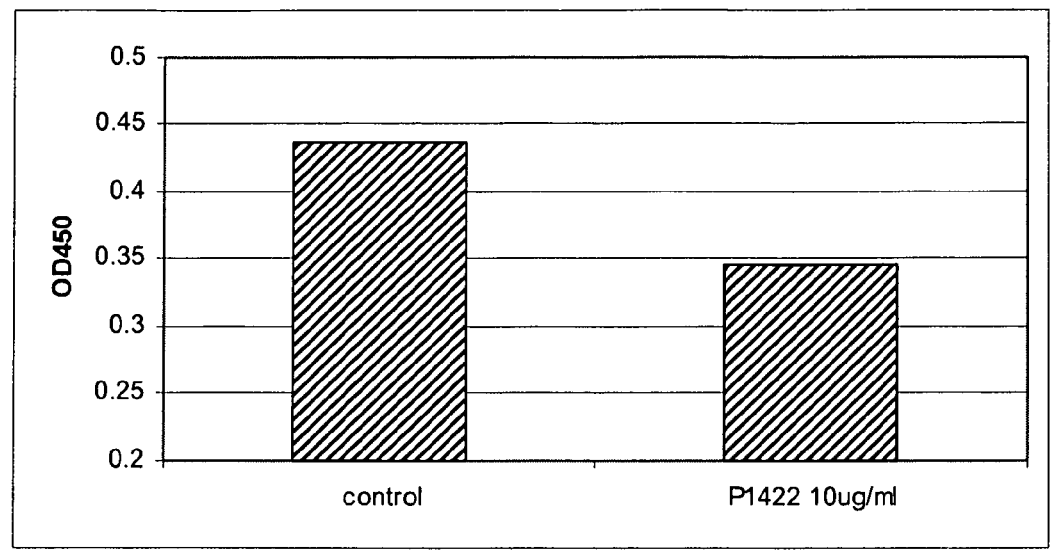
FIG. 3 shows the effect of tetrapeptides P1422 (SEQ ID NO:1) (A) and P1423 (SEQ ID NO:2) (B) at 10 μg/mL on IL-6 induction in keratinocytes treated with UVB. "Control" denotes cells that were UVB-irradiated, but did not receive peptide. "OD450" denotes relative IL-6 expression as measured by ELISA. Refer to Example 4.
Figure 3:
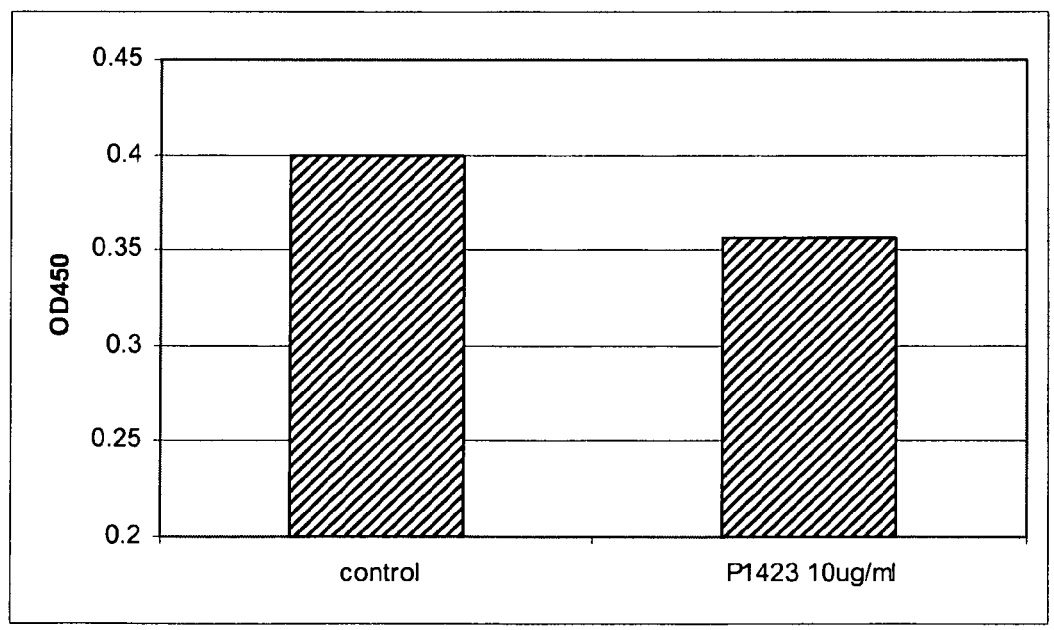

Screening Peptides for Anti-inflammatory Activity: Inhibition of UV-induced IL-6 Expression in Human skin Keratinocytes and Fibroblasts It is well known that UV-irradiated epidermal keratinocytes and fibroblasts release pro-inflammatory cytokines. Therefore these cells, besides skin epithelial cells, may contribute to the cascade of events resulting in the debilitating effects of photoaging. For these reasons, P1422 (SEQ ID NO:1) and P1423 (SEQ ID NO:2) were tested for inhibitory activity toward UV-induced IL-6 expression in these cell types. As shown in FIGS. 3 (A and B), both these tetrapeptides down-regulate IL-6 expression in UVB-treated human keratinocytes.

Such peptide-mediated IL-6 down-regulation was also evident in human fibroblasts after exposure to UVB. P1423 (SEQ ID NO:2)-mediated inhibition of IL-6 expression is dose-dependent, as the peptide at 2, 5 and 10 µg/mL reduced IL-6 levels by 24, 30 and 48%, respectively, compared to control cell IL-6 production (no peptide treatment, data not shown). At 10 µg/mL, P1422 (SEQ ID NO:1) reduced UV-stimulated IL-6 expression in fibroblasts by 30% compared to control cell IL-6 production; however, no significant reduction of IL-6 was observed when lower concentrations of the peptide were applied.

Example 5

Screening Peptides for Anti-inflammatory Activity: Inhibition of UV-induced MMP-1 Expression in Human Skin Fibroblasts UV (UVA and UVB) irradiation increases MMP-1 expression and activation in fibroblasts. Most MMPs produced in human skin in response to UV exposure are derived from resident fibroblasts. Since MMP production contributes to UV-induced inflammatory reactions in skin (e.g., edema) and the chronic effects thereof (e.g., wrinkling), inhibition of fibroblast MMP-1 expression should alleviate the negative effects of sunlight on skin.

Figure 4:
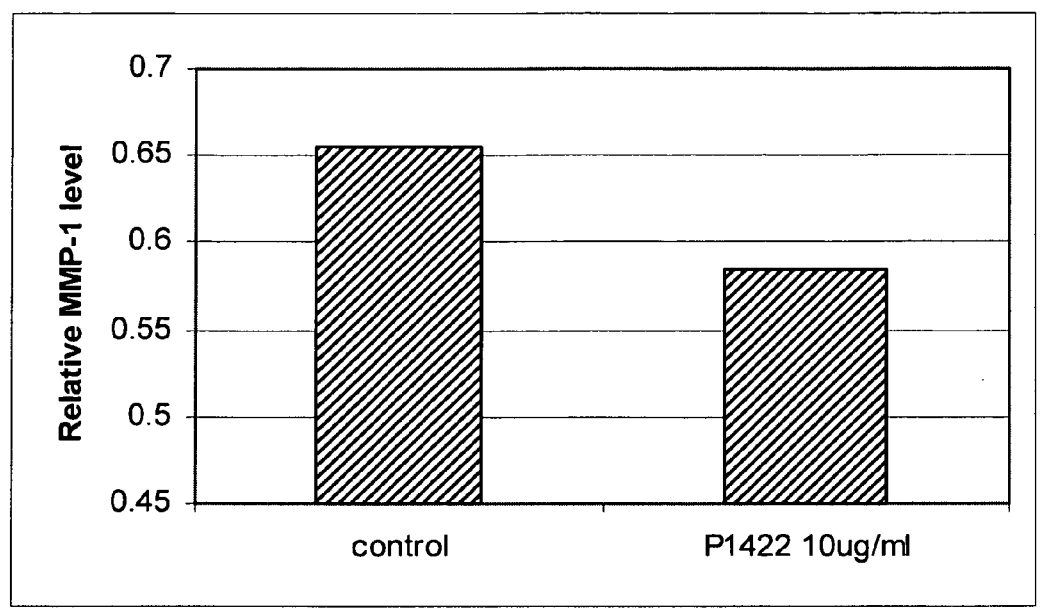
FIG. 4 shows the effect of tetrapeptides P1422 (SEQ ID NO:1) (A) and P1423 (SEQ ID NO:2) (B) at 10 μg/mL on MMP-1 induction in skin fibroblasts treated with UVA. The relative amount of MMP-1 produced by each culture was determined using ELISA-generated OD450 absorption values. "Control" denotes cells that were UVA-irradiated, but did not receive peptide. Refer to Example 5.
Figure 4:
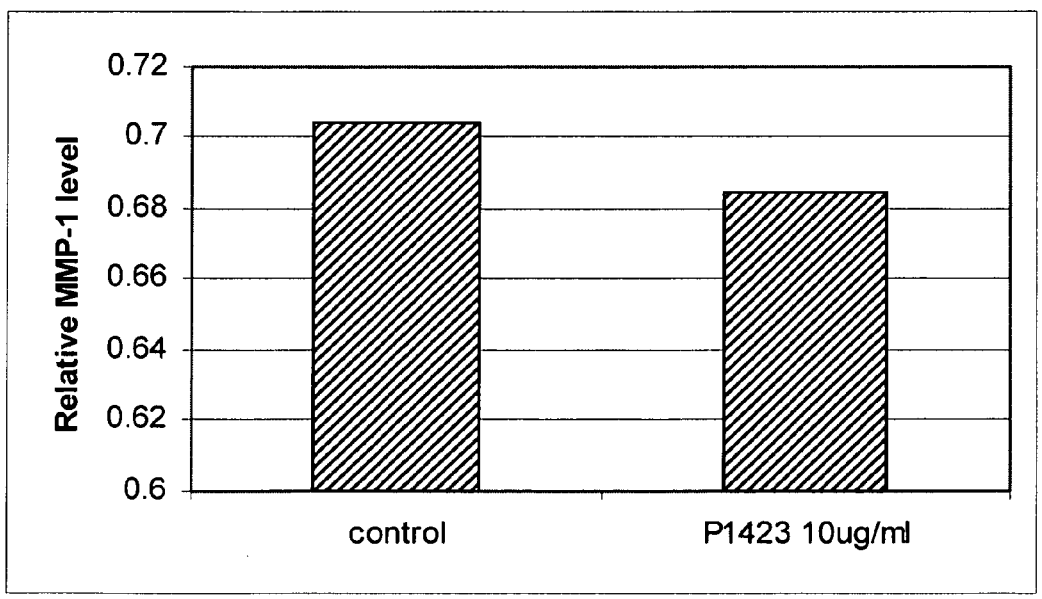

With this in mind, experiments were performed to determine the effects of the tetrapeptides P1422 (SEQ ID NO:1) and P1423 (SEQ ID NO:2) on UV-induced MMP-1 expression in fibroblasts. After UVA treatment (500 µW/cm$^2$) for 45 seconds, fibroblasts were treated with or without these peptides. Both P1422 (SEQ ID NO:1) and P1423 (SEQ ID NO:2) at 10 µg/mL were able to down-regulate UVA-induced MMP-1 expression, as shown in FIGS. 4 (A and B).

Figure 5:
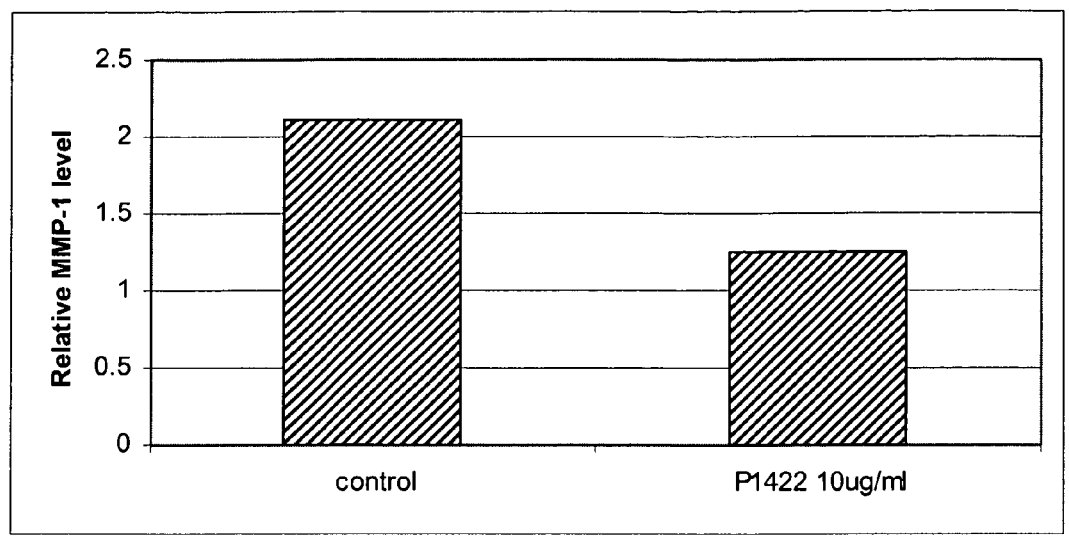
FIG. 5 shows the effect of tetrapeptides P1422 (SEQ ID NO:1) (A) and P1423 (SEQ ID NO:2) (B) at 10 μg/mL on MMP-1 induction in skin fibroblasts treated with media conditioned by UVB-treated keratinocytes. The relative amount of MMP-1 produced by each culture was determined using ELISA-generated OD450 absorption values. "Control" denotes cells that were incubated in media conditioned by UVB-irradiated keratinocytes, but which did not receive peptide. Refer to Example 5.
Figure 5:
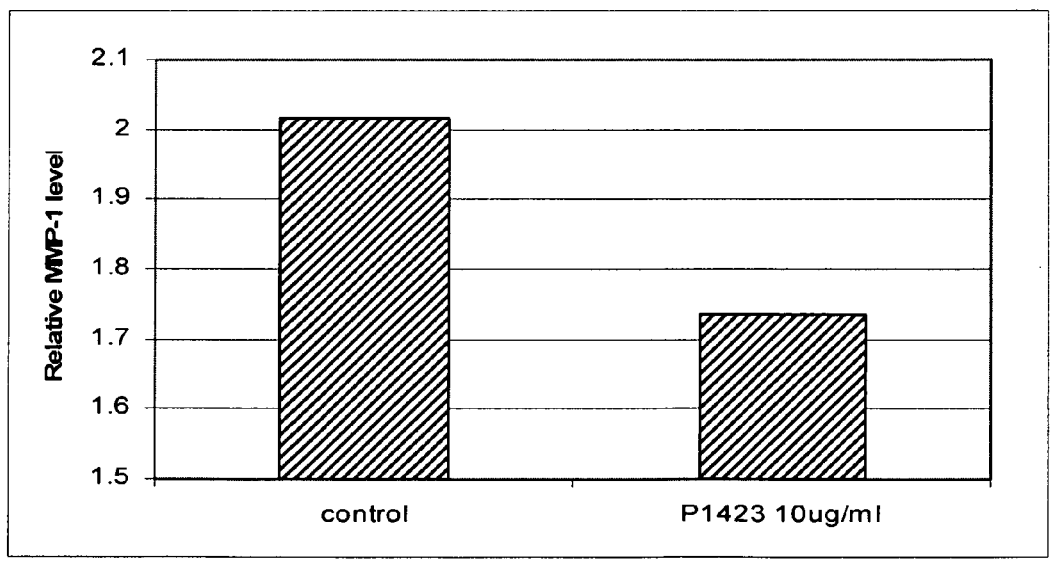

Fagot et al. (2002, 2004) have shown that cytokines produced by UVB-stimulated keratinocytes effect paracrine upregulation of MMP-1 in dermal fibroblasts. This mode of signaling was modeled experimentally by incubating fibroblasts in media conditioned by UVB-treated keratinocytes. Though MMP-1 was upregulated in fibroblast cultures treated in this manner, those cultured with either tetrapeptide P1422 (SEQ ID NO:1) or P1423 (SEQ ID NO:2) exhibited far less MMP-1 induction (FIGS. 5A and B).

In conclusion, these studies show that certain tetrapeptides based on the TRAF6-binding domain are capable of down-regulating the level of IL-6 and MMP-1 induced by UV radiation. These findings are surprising, since these inflammatory pathways, as induced by UV radiation, have not previously been known to involve TRAF6-related signaling events. The inhibition of both a main inflammatory mediator (IL-6) and effector (MMP-1) by these short peptides demonstrates their applicability to the prevention and treatment of skin inflammation and its deleterious effects.

Example 6

Invention Embodiments Incorporating a Protease Inhibitor

The instant invention is also directed to skin care formulations containing protease inhibitors in combination with bioactive peptides. Such compositions would be expected to exhibit cosmetic and therapeutic activity toward the skin and other epithelial surfaces (e.g., mucosal surfaces). Serine protease inhibitors are an example component of the invention. Methods of using compositions containing bioactive peptides and protease inhibitors to effect therapeutic and cosmetic changes in skin are another aspect of the instant invention.

A wide range of peptide ingredients are used in the cosmetic and skin care industry to deliver an array of bioactivities onto and into the skin (Table 2). It has been well documented that the outer layer of the skin, the stratum corneum (SC), contains an array of proteases capable of degrading proteins and peptides. The bioactivities of certain peptides when applied to the skin are exerted in the SC. Thus, proteases located in the SC constitute a barrier to achieving the full therapeutic and/or cosmetic benefits of topical skin applications that comprise bioactive peptides.

The SC contains at least three families of proteases: serine, cysteine and aspartate proteases. The serine proteases (SP) include the epidermal-specific proteases kallikrein-5 (also known as SC tryptic enzyme, SCTE) (Brattsand and Egelrud, 1999) and kallikrein-7 (also known as SC chymotryptic enzyme) (Hansson et al., 1994). Both these kallrikreins are known to be involved in desquamatory processes (i.e., shedding of the skin). Additional serine proteases that have been isolated in the skin are plasmin and urokinase (Voegeli et al., 2007). SC thiol protease (SCTP) and cathepsin D are some of the cysteine and aspartate proteases, respectively, present in the SC (Bernard et al., 2003; Horikoshi et al., 1998).

Seasonal variation in the biophysical and biological characteristics of the SC are well documented. In particular, the winter season has been shown to more severely affect the properties of exposed skin versus routinely covered skin. Moreover, when compromised, such as in dry skin conditions, facial SC has been shown to contain increased levels of pro-inflammatory cytokines and proteases. Voegeli et al. (2007) examined the distribution of key serine protease activities (kallikrein-5, kallikrein-7, urokinase, plasmin and a tryptase-like enzyme) in different layers of the SC of the cheek and forearm by analyzing consecutive tape strippings of healthy Caucasian subjects during winter and summer. Compared to the activity levels observed in forearm SC, the activity levels of plasmin, urokinase and tryptase on the face were approximately five to eight times higher, while the activity levels of kallikreins-5 and -7 on the cheek were approximately two to four times higher. Thus, protected skin areas show less protease activity than those areas that are exposed to the environment, possibly indicating subclinical inflammation in exposed skin. The following insights were also made by Voegeli et al. (2007): (i) in normal healthy forearm skin, the outer SC exhibits greater serine protease activity than in its deeper layers; (ii) compared with the forearm, urokinase- and plasmin-like activities are elevated on SC strippings from the cheek, confirming activation of the plasminogen cascade; and (iii) tryptase-like activity in the SC is also elevated in samples from the cheek, possibly indicating involvement of mast cells in barrier-compromised skin and/or the synthesis of a novel tryptase-like enzyme by keratinocytes. As there is an elevation of urokinase, plasmin, kallikrein-5, kallikrein-7 and tryptase-like enzyme activities observed in SC derived from skin of clinically normal cheeks, it is anticipated that even higher activities of these enzymes will exist under skin conditions where the epidermal barrier is impaired.

There have been a number of recent studies linking proteases present in the SC to clinical conditions of the skin such as rosacea and psoriasis (Borgono et al., 2007; Yamasaki et al., 2007; Pampalakis and Sotiropoulou, 2007). In these cases, the proteases in question are the trypsin-like and chymotrypsin-like serine proteases of the kallikrein family. The role of proteases in rosacea may partly be based upon the breakdown of the host innate immunity peptide LL-37 into pro-inflammatory fragments (Yamasaki et al., 2007). With psoriasis, the kallikrein proteases responsible for desquamation of superficial cells escape from regulation and cause an increase in desquamation leading to scaling, which occurs from over-shedding of skin. These conditions lead to inflammation and other significant clinical symptoms. At a sub-clinical level these processes can lead to dry skin, reddened skin, a breakdown in barrier function (leading to loss of skin moisture), a breakdown of extracellular matrix and premature skin aging. Therefore, the use of active ingredients capable of slowing this process by inhibiting skin proteases is of significant value.

Peptide active ingredients are used in cosmetic and skin care products to provide bioactivity capable of improving the appearance, feel and aesthetics of skin. Such bioactive peptides can also be used for therapeutic purposes, such as in the treatment of wounds or burns. However, as described above, the skin expresses proteases capable of degrading proteins and peptides, thus impeding the ability of certain peptides to exert their salutary effects. This negative effect of SC-residing proteases is in addition to the negative effects thereof with regard to inflammation and skin cell turnover. These problems are overcome by this aspect of the present invention, which is drawn in part to formulations comprising both a bioactive peptide and a protease inhibitor. Such a combination renders skin care formulations with three desirable features: (i) the peptide component provides a specific bioactivity (e.g., anti-inflammation, cell stimulation/proliferation/migration, etc. . . . ); (ii) the protease inhibitor component protects the peptide component from degradation, resulting in prolonged salutary peptide effects; and (iii) the protease inhibitor component reduces the general negative effects of proteases toward the skin, such as redness and scaling. This last feature (iii) in part entails the protection of bioactive peptides that are endogenous to the site of application of the formulation; thus, the protease inhibitor enhances the activities of both the ectopically applied peptide and those peptides that are naturally expressed by the skin.

The instant invention provides an innovative strategy for enhancing the activity of peptides in therapeutic and cosmetic preparations. Such peptide functional enhancement is obtained by combining a peptide of interest with appropriate protease inhibitors. Not only does the protease inhibitor act to prolong therapeutic activity by increasing peptide half-life, but the inhibitor also prevents the production of pro-inflammatory fragments from native skin proteins. Such a combination of peptide and protease inhibitor thus provides a skin care formulation with a three-tiered level of efficacy. While each component—the peptide and the protease inhibitor—delivers its own salutary effect, their combination synergizes to render the formulation as much more potent than a formulation having only one these components.

The present invention also provides a substantial cost benefit. A peptide used in combination with an appropriate protease inhibitor will exhibit a greater half-life. Therefore, such a peptide need not be supplied at the higher levels required when the peptide is used in the absence of protease inhibitor. The cost of protease inhibitors for preparing the bioactive peptide formulation of the present invention is significantly less than the cost of producing the higher amounts of peptide that would be necessary to achieve the activity level of the formulation.

Bioactive peptides are well known in the art; those which can be incorporated in this aspect of the invention are preferably less than 200 amino acid residues in length, less than 100 amino acid residues in length, less than 50 amino acid residues in length, less than 45 amino acid residues in length, less than 40 amino acid residues in length, less than 35 amino acid residues in length, less than 30 amino acid residues in length, less than 25 amino acid residues in length, less than 20 amino acid residues in length, less than 15 amino acid residues in length, or less than 10 amino acid residues in length. Other bioactive peptides that can be used in the present invention are preferably at least 4, 5, 6, 7, 8, or 9 amino acid residues in length.

Non-limiting examples of bioactive peptides that can be incorporated in various embodiments of the subject invention are numerous and are described in U.S. Pat. No. 6,255,282 (see FIGS. 3A/B and the claims therein), U.S. Pat. No. 6,303,568 (see Table 1 therein), U.S. Pat. No. 5,962,410 (see Table 1 therein), U.S. Pat. No. 7,875,744 (see Table 1 and the claims therein), U.S. Pat. No. 7,407,940 (see Table 1 and the claims therein), U.S. Appl. Publ. No. 20070299015 (appl. Ser. No. 11/811,876) (see Tables 1, 5 and the claims therein), appl. Ser. No. 12/005,653 (see Table 1 and the claims therein), U.S. Pat. No. 6,288,212 (see Table 1 and the single claim therein), U.S. Pat. No. 6,337,317 (see claims therein), U.S. Pat. No. 6,172,185 (see Table 1 and the claims therein), and appl. Ser. No. 61/000,815 (see Table 1 and the claims therein); each of these patents and applications, especially the indicated sections thereof, are herein incorporated by reference in their entirety. The tetrapeptides disclosed in the present application (Table 1 and SEQ ID NOs:14-15) can also be incorporated in this aspect of the invention. One or more bioactive peptides may be used in the invention. Although the invention is mainly drawn to the incorporation of peptides having an inherent activity, which may or may not be dependent on the environs in which the peptide is placed (i.e., the peptide is only active when placed in a particular context), peptides that do not have (or are not known to have) any particular activity may also be used in the invention.

Other non-limiting examples of bioactive peptides that can be incorporated in various embodiments of the subject invention are listed in Table 2.

TABLE 2

Certain peptides currently marketed for inclusion as active ingredients in skin care products.[a]

| COMPANY[b] | NAME | ACTIVITY | PREMIX PRODUCTS | SOURCE |
|---|---|---|---|---|
| Atrium | Tripeptide-2 | ECM stimulation via MMP-1 inhibition | ECM-protect ® | Undisclosed |
| Atrium | Tripeptide-1 | ECM stimulation via growth factor | Kollaren ® | HGF |
| Atrium | Acetyl Tetrapeptide-2 | Reduce loss of thymic factors | Thymulen ® 4 | Thymopoieten |
| Atrium | Acetylpeptide-1 | Melanin increase via MSH regulation | Melitane ® | MSH agonist |
| Atrium | Nonapeptide-1 | Tyrosinase activation inhibition | Melanostatine ® | MSH antagonist |
| Grant Indust. | Palmitoyl Hexapeptide-6 | Dermal repair | Matrix Rebuilder ™ | Innate immunity |
| Grant Indust. | Oligopeptide-10 | Dermal protection | InvisaSkin-64 ™ | Innate immunity |
| Lipotec | Tripeptide-1 | Inhibits collagen glycation | Aldenine ®, Trylagen ™ | Human serum |
| Lipotec | Tripeptide-10 Citrulline | Collagen fibrillogenesis | Decorinyl, Trylagen ™ | Decorin |
| Lipotec | Acetyl Tetrapeptide-5 | edema reduction by ACE inhibition | Eyeseryl ® | Undisclosed |
| Lipotec | Pentapeptide-3 | Botox-like via mimicking enkephalins | Leuphasyl ® | Undisclosed |
| Lipotec | Acetyl Hexapeptide-3 (or-8) | Botox-like via SNARE inhibition | Argireline ® | SNAP-25 |

TABLE 2-continued

Certain peptides currently marketed for inclusion as active ingredients in skin care products.[a]

| COMPANY[b] | NAME | ACTIVITY | PREMIX PRODUCTS | SOURCE |
|---|---|---|---|---|
| Lipotec | Acetyl Octatapeptide-1 | Botox-like via SNARE inhibition | SNAP-8 | SNAP-25 |
| Lipotec | Hexapeptide-10 | Increases cell proliferation and laminin V | Serilesine ® | Laminin |
| Pentapharm | Palmitoyl Tripeptide-5 | Collagen synthesis via TGF-beta | Syn ®-coll | Thrombospondin I |
| Pentapharm | Dipeptide Diaminobutyroyl Benzylamide Diacetate | Botox-like via acetycholine receptor | Syn ®-ake | Waglerin 1 |
| Pentapharm | Oligopeptide-20 | MMP inhibitor via TIMP | Pepha ®-timp | TIMP-2 |
| Pentapharm | Pentapeptide-3 | Botox-like via acetycholine receptor | Vialox ® | Undisclosed |
| Procyte | Copper GHK/AHK | Wound healing | Brand example Neova | Human serum |
| Sederma | Dipeptide-2 | Lymph drainage via ACE inhibition | Eyeliss ™ | Rapeseed |
| Sederma | Palmitoyl Oligopeptide | Collagen synthesis via signaling | Eyeliss ™, Matrixyl ™ 3000 | Human serum |
| Sederma | Palmitoyl Tetrapeptide-7 (formally-3) | Elasticity via IL6 reduction | Matrixyl 3000 ™, Rigin ™ | IgG/matrikine |
| Sederma | Palmitoyl Pentapeptide-3 | Collagen stimulation via signaling | Matrixyl ™ | Procollagen |
| Sederma | Palmitoyl Oligopeptide | Retinoic acid-like activity | Biopeptide-CL ™ | Collagen |
| Sederma | Palmitoyl Oligopeptide | Increases collagen and HA | Biopeptide-EL ™ | Elastin |

[a]Abbreviations used in table: ACE, angiotensin I converting enzyme; ECM, extracellular matrix; HA, hyaluronic acid; HGF, hepatocyte growth factor; MMP, matrix metalloproteinases; MSH, melanocyte stimulating hormone; SNARE, soluble NSF attachment receptor (NSF, N-ethyl-maleimide sensitive factor); TGF-β, transforming growth factor-β; TIMP, tissue inhibitor of MMP.
[b]Manufacturer location: Atrium Biotechnologies (Quebec City, Canada), Grant Industries (Elmwood, NJ), Lipotec (Barcelona, Spain), Pentapharm (Basel, Switzerland), Procyte (Photomedix, Montgomeryville, PA), Sederma (Le Perray en Yvelines, France).

Study Aim

The use of protease inhibitors in cosmetic and therapeutic skin care products in combination with bioactive peptides to generate multiple benefits has not been explored. Thus, the instant inventors aimed to determine if protease inhibitors could protect bioactive peptides—both synthetically and innately derived—from proteolytic degradation. Such protease inhibitors would be candidates for use in peptide-containing skin care formulations.

Assay Materials and Methodology

The following protease inhibitors were characterized for the ability to block the breakdown of bioactive peptides under certain proteolytic conditions: aprotinin (Sigma-Aldrich, St. Louis, Mo.), tranexamic acid (Sigma-Aldrich), benzamidine (Sigma-Aldrich), Fmoc-lys(Boc) (Chem-Impex, Chicago, Ill.), Fmoc-arg(Pmc) (Chem-Impex), benzoyl-arg-nitroanilide (Sigma-Aldrich) and benzoyl-arg-naphthylamide (Sigma-Aldrich).

The following peptides were used as representative skin care bioactive ingredient peptides and innate skin peptides: oligopeptide-10 (HB64) (Peptisyntha, Torrence, Calif.), the sequence of which is FAKALKALLKALKAL-NH$_2$ (SEQ ID NO:17) (refer to U.S. Pat. No. 7,381,704); hexapeptide-21 (HB168) (Neo-MPS, San Diego, Calif.), the sequence of which is FALLKL-NH$_2$ (SEQ ID NO:18) (refer to U.S. Pat. No. 7,381,704); HB1345 (Peptisyntha), the sequence of which is decanoyl-KFKWPW-NH$_2$ (SEQ ID NO:19) (refer to U.S. Pat. No. 7,407,940); and LL-37 (LLGDFFRK-SKEKIGKEFKRIVQRIKDFLRNLVPRTES, SEQ ID NO:20), which is disclosed by Johansson et al. (1998) (herein incorporated by reference in its entirety). While the HB64, HB168 and HB1345 peptides have a synthetic origin, LL-37 was originally characterized to be innately expressed by human cells.

The following proteases were employed in reducing the instant invention to practice: chymotrypsin (Sigma-Aldrich), which cleaves amino acid chains at the carboxyl side of tyrosine, tryptophan, and phenylalanine; trypsin (Sigma-Aldrich), which cleaves amino acid chains at the carboxyl side of lysine and arginine, except when either is followed by proline; elastase (Sigma-Aldrich), which is a serine protease that cleaves amino acid chains at the carboxy side of small, hydrophobic amino acids such as glycine, alanine, and valine; kallikrein (Sigma-Aldrich), which is a serine protease); plasmin (Sigma-Aldrich), which is a serine protease; and urokinase, which is a serine protease.

Procedures for Measuring Peptide Degradation

Peptides of synthetic origin and LL-37 were used in the protease processing experiments at a concentration of 1-2 mg/mL in 0.5M MOPS pH 8.5/0.5M NaCl final buffer concentration. Proteases were used at a concentration of 0.020-0.050 mg/mL.

Experiments were run in pairs, one with protease inhibitor and one without a protease inhibitor. Liquid chromatography/mass spectrometry (LC/MS) spectra were collected at approximately 1-minute, 1-hour, 4-hour and 24-hour time points from the time of adding protease to the peptide (time zero). LC/MS spectra were collected using a standard reverse phase gradient starting at 5% acetonitrile and ramping up to 65% acetonitrile in 25 minutes. Peptide parent ions were monitored with XIC (eXtracted Ion Count) traces, whereas peptide fragments were observed with TIC (Total Ion Count) traces, as discussed below.

The proteases employed in the study were initially dissolved in a 1M NaCl solution, while the peptides were dissolved in 1M MOPS buffer at pH 8.5. The solutions were equilibrated to 37° C. and then mixed at a ratio of 1:1 to start each experiment. Lower buffer concentrations were also used (0.1M MOPS pH 8.5 and 0.2M NaCl). Protease inhibitors were tested at several different concentrations (low and high from 0.02 mg/mL to 40 mg/mL) against a given protease.

Certain mass spectrometry procedures used in this study are discussed below for instructional purposes to describe how the data in Table 3 (below) were generated and interpreted. Three different data outputs were obtained using mass spectrometry in monitoring the inventive method:

A. TIC trace (Total Ion Count), which is a readout of all molecular weights (all molecules) passing through the column/mass spectrometer in a specific time period.

B. XIC trace (eXtracted Ion Count), which is a readout representing the pulling out of a specific molecular weight from the TIC trace.

C. A mass spectrum, which represents a range of molecular entities within the peak selected from the TIC or XIC trace.

Since these procedures are well known in the art, the below discussion will be limited to describing the results observed in the mass spectrometry experiments (i.e., data not shown).

Results

The following examples demonstrate how the different mass spectrometry outputs described above can be used to monitor protease-mediated degradation, and inhibition thereof, of synthetic (e.g., HB64) and innate immunity peptides (e.g., LL-37). The mass spectrometer used in these studies has a limit of detection below which the specific molecular weight of a molecule cannot be identified from the TIC trace. In these below-detection situations, it was assumed that the tested peptide was completely degraded.

TIC traces were obtained to follow the degradation/digestion of Oligopeptide-10 (HB64) by the protease trypsin over a 23-hour period of time. Specifically, peptide degradation was measured by LC/MS at time zero, 1 hour and 23 hours. It was clear that the parent peak (represents the full-length, non-degraded peptide) in the TIC traces was reduced over time and peaks for various breakdown products increased in intensity over time. A primary digestion product of this trypsin-mediated proteolysis is the tetrapeptide ALLK (SEQ ID NO:21).

Interestingly, the TIC traces showed that in a repeat experiment that included the protease inhibitor aprotinin, the parent peptide was protected against degradation by the protease. This result is consistent with the expectation that a bioactive peptide would retain its structure, and therefore its function, for a longer period of time when applied to the skin in combination with a protease inhibitor. The instant invention would therefore be more effective compared to skin formulations containing a bioactive peptide alone at the same concentration. Also, even if the chosen bioactive peptide might not be subject to proteolytic degradation for reasons of length and/or sequence, the inclusion of a protease inhibitor would prevent the degradation of salutory peptides that are naturally expressed at the site of formulation application (i.e., beneficial endogenous peptides would be protected).

A TIC trace of peptide LL-37 that had been exposed to plasmin for only 1 minute served to render a time zero readout. The presence of intact LL-37 peptide was detected at approximately the 16-minute retention time as confirmed by a mass spectrum readout; three distinct peaks at 899.5, 1123.4 and 1497.6 amu (atomic mass units) represented different charge forms, respectively, of the same peptide (LL-37).

After a 1-hour incubation with plasmin, the molecular weight of parent peptide LL-37 was undetectable and TIC trace peaks with a lower retention time (11 minutes to 13 minutes) appeared. These peaks represent breakdown products of LL-37 with molecular weights as low as 450. The exact sequence of one of the breakdown products of LL-37 that was detected was determined to be RIVQRIKDFLRN-LVPRTES (SEQ ID NO:22) based on a unique match in molecular weight to this LL-37 portion. Three different charge forms of SEQ ID NO:22 were observed, just as what had been observed with full-length LL-37.

The above experiment with LL-37 and plasmin was repeated, but this time including the protease inhibitor tranexamic acid in the reaction. A TIC trace of this reaction after a 1-hour incubation period obtained. A mass spectrum taken at the retention time of approximately 16.5 minutes. As was evident in both the TIC trace and mass spectrum, breakdown products of LL-37 were produced; importantly however, the complete, intact, parent peptide was still detectable at appreciable levels as three mass spectral peaks, given charge differences. This result is consistent with the results of the above analysis using a different peptide/protease/inhibitor set. Thus, this aspect of the current invention would be expected to be applicable to various combinations of bioactive peptides and protease inhibitors; this expectation is further corroborated with the below-presented evidence in Table 3.

In another experiment, the degradation of Oligopeptide-10 (HB64) after a 4-hour exposure to plasmin was monitored with TIC and XIC traces. From this analysis, it was evident that plasmin targets and degrades HB64. The XIC trace (at 799.5 amu) showed that, while most of the HB64 peptide was degraded, some parent peptide could still be detected. When this reaction included tranexamic acid, it was evident from the TIC and XIC traces that the HB64 peptide was protected from plasmin-mediated proteolysis. In fact, the amount of parental peptide in the reaction as determined by an XIC trace was five-times greater compared to when the peptide was incubated with plasmin alone.

A series of experiments were performed employing the above-described methodology to determine the utility of the invention as it regards a wider range of proteases, peptides and protease inhibitors. Data from this work are summarized in Table 3. If, at any specific time-point, there was no detectable parent peptide (i.e., the absence of non-degraded peptide), then that time-point was documented as the time required for peptide degradation.

TABLE 3

The protective effects of various protease inhibitors toward various bioactive peptides.

| Protease | Conc. μg/mL | Peptide[a] | MW | Protease Inhibitor | Conc. mg/mL | Survival | Expt. No. |
|---|---|---|---|---|---|---|---|
| Trypsin | 25 | HB64 | 1598 | none | | <1 hr | 4 |
| Trypsin | 25 | HB64 | 1598 | aprotinin | 0.02 | >24 hr | 5 |
| Trypsin | 25 | HB168 | 702 | none | | <1 hr | 6 |
| Trypsin | 25 | HB168 | 702 | aprotinin | 0.02 | >24 hr | 7 |
| Trypsin | 25 | HB1345 | 1044 | none | | <1 hr | 8 |
| Trypsin | 25 | HB1345 | 1044 | aprotinin | 0.02 | >24 hr | 9 |
| Trypsin | 25 | HB64 | 1598 | none | | <1 hr | 10 |
| Trypsin | 25 | HB64 | 1598 | ursolic Acid | 0.02 | <1 hr | 11 |
| Trypsin | 25 | HB64 | 1598 | none | | <1 hr | 12 |

TABLE 3-continued

The protective effects of various protease inhibitors toward various bioactive peptides.

| Protease | Conc. µg/mL | Peptide[a] | MW | Protease Inhibitor | Conc. mg/mL | Survival | Expt. No. |
|---|---|---|---|---|---|---|---|
| Trypsin | 25 | HB64 | 1598 | tranexamic acid | 0.02 | <1 hr | 13 |
| Trypsin | 25 | HB64 | 1598 | Fmoc-Lys(Boc) | 0.02 | <1 hr | 14 |
| Trypsin | 25 | HB64 | 1598 | Fmoc-Arg(Pmc) | 0.02 | <1 hr | 15 |
| Trypsin | 25 | HB64 | 1598 | benzamidine | 0.02 | <1 hr | 16 |
| Trypsin | 25 | HB64 | 1598 | benzamidine | 0.80 | >24 hr | 17 |
| Trypsin | 25 | HB64 | 1598 | tranexamic acid | 0.80 | <1 hr | 18 |
| Trypsin | 25 | HB64 | 1598 | benzoyl-Arg-nitroanilide | 0.80 | <1 hr | 19 |
| Trypsin | 25 | HB64 | 1598 | benzoyl-Arg-naphthylamide | 0.80 | >24 hr | 20 |
| Trypsin | 25 | HB64 | 1598 | ursolic Acid | 0.80 | <24 hr | 21 |
| Elastase | 25 | HB64 | 1598 | none | | <1 hr | 22 |
| Elastase | 25 | HB64 | 1598 | aprotinin | 0.02 | <1 hr | 23 |
| Elastase | 25 | HB64 | 1598 | tranexamic acid | 0.80 | <1 hr | 24 |
| Plasmin | 25 | HB64 | 1598 | none | | <4 hr | 25 |
| Plasmin | 25 | HB64 | 1598 | tranexamic acid | 0.80 | <24 hr | 26 |
| Kallikrein | 25 | HB64 | 1598 | none | | <24 hr | 27 |
| Kallikrein | 25 | HB64 | 1598 | tranexamic acid | 0.80 | <24 hr | 28 |
| Plasmin | 25 | HB64 | 1598 | tranexamic acid | 0.80 | <6 hr | 29 |
| Plasmin | 25 | HB64 | 1598 | none | | <6 hr | 30 |
| Plasmin | 50 | HB64 | 1598 | tranexamic acid | 10 | <6 hr | 31 |
| Plasmin | 46 | HB64 | 1598 | none | | <4 hr | 32 |
| Trypsin | 22 | HB64 | 1598 | tranexamic acid | 10 | <1 hr | 33 |
| Chymotrypsin | 25 | HB64 | 1598 | none | | <1 hr | 34 |
| Chymotrypsin | 25 | HB64 | 1598 | aprotinin | 0.02 | <24 hr | 35 |
| Plasmin | 22 | LL-37 | 4493 | tranexamic acid | 9 | <4 hr | 36 |
| Plasmin | 22 | LL-37 | 4493 | none | | <1 hr | 37 |
| Plasmin | 22 | LL-37 | 4493 | none | | <45 min | 38 |
| Chymotrypsin | 22 | LL-37 | 4493 | none | | <1 hr | 39 |
| Chymotrypsin | 22 | LL-37 | 4493 | tranexamic acid | 9 | <1 hr | 40 |
| Kallikrein | 22 | LL-37 | 4493 | none | | <4 hr | 41 |
| Kallikrein | 22 | LL-37 | 4493 | tranexamic acid | 9 | <4 hr | 42 |
| Plasmin | 20 | HB64 | 1598 | none | | NA | 43 |
| Plasmin | 20 | HB64 | 1598 | tranexamic acid | 40 | NA | 44 |
| Plasmin | 20 | HB64 | 1598 | none | | <4 hr | 45 |
| Plasmin | 22 | HB64 | 1598 | tranexamic acid | 40 | <24 hr | 46 |
| Kallikrein | 22 | LL-37 | 4493 | none | | <4 hr | 47 |
| Kallikrein | 22 | LL-37 | 4493 | aprotinin | 0.02 | <24 hr | 48 |
| Kallikrein | 22 | LL-37 | 4493 | none | | <1 hr | 49 |
| Kallikrein | 22 | LL-37 | 4493 | tranexamic acid | 40 | <2 hr | 50 |
| Urokinase | 22 | LL-37 | 4493 | none | | <24 hr | 51 |
| Urokinase | 22 | LL-37 | 4493 | aprotinin | 0.02 | >24 hr | 52 |
| Urokinase | 22 | LL-37 | 4493 | none | | <24 hr | 53 |
| Urokinase | 22 | LL-37 | 4493 | tranexamic acid | 40 | >24 hr | 54 |
| Kallikrein | 22 | LL-37 | 4493 | none | | <1 hr | 55 |
| Kallikrein | 22 | LL-37 | 4493 | tranexamic acid + Ursolic acid | 20 each | >24 hr | 56 |
| Kallikrein | 22 | LL-37 | 4493 | 10% DMSO | | <1 hr | 57 |

[a]All peptides were used at a final concentration of 1 mg/mL.

SUMMARY

As noted in this example, some of the most important proteases in relation to skin and peptide breakdown are plasmin, kallikrein and urokinase. The instant invention was shown to work against these proteases (e.g., Table 3). Importantly, the tested protease inhibitors have excellent safety profiles. For example, aprotinin and tranexamic acid are employed as systemic drugs for clotting therapy, while ursolic acid is used as a cosmetic and herbal ingredient. The goal here was to identify an agent (or agents) capable of protecting innate and synthetic peptides from proteolytic degradation; such inhibitors would be useful in combination with bioactive peptides in skin care products. Given the inhibitory activity of tranexamic acid against a broad spectrum of proteases, coupled with its low cost of manufacture, safety profile and solubility, tranexamic acid is a preferred protease inhibitor for practicing this aspect of the instant invention.

All of the compositions or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the methods described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the scope of the invention.

All patents and publications identified in this application are hereby incorporated by reference in their entirety.

REFERENCES

Bernard D et al. (2003), Analysis of proteins with caseinolytic activity in a human stratum corneum extract revealed a yet unidentified cysteine protease and identified the co-called "stratum corneum thiol protease" as cathepsin L2, *J. Invest. Dermatol.* 120:592-600.

Borgono C A et al. (2007), A potential role for multiple tissue kallikrein serine proteases in epidermal desquamation, *J. Biol. Chem.* 282: 3640-3652.

Brattsand M and Egelrud T (1999), Purification, molecular cloning, and expression of a human stratum corneum trypsin-like serine protease with possible function in desquamation, *J. Biol. Chem.* 274:30033-30040.

Hansson L et al. (1994), Cloning, expression, and characterization of stratum corneum chymotryptic enzyme. A skin-specific human serine proteinase, *J. Biol. Chem.* 269:19420-19426.

Horikoshi T et al. (1998), Isoforms of cathepsin D and human epidermal differentiation, *Biochimie* 80:605-612.

Johansson J et al. (1998), Conformation-dependent antibacterial activity of the naturally occurring human peptide LL-37, *J. Biol. Chem.* 273:3718-3724.

Pampalakis and Sotiropoulou (2007), Tissue kallikrein proteolytic cascade pathways in normal physiology and cancer, *Biochim. Biophys. Acta.* 1776:22-31.

Voegeli R et al. (2007), Profiling of serine protease activities in human stratum corneum and detection of a stratum corneum tryptase-like enzyme, *Int. J. Cosmet. Sci.* 29:191-200.

Yamasaki K et al. (2007), Increased serine protease activity and cathelicidin promotes skin inflammation in rosacea, *Nat. Med.* 13:975-980.

What is claimed is:

1. An isolated peptide, wherein the amino acid sequence of the peptide consists of proline-glutamine-glutamate-X (P-Q-E-X), wherein X is lysine (K) or isoleucine (I), wherein the isolated peptide is optionally modified.

2. The peptide of claim 1, wherein the peptide is amidated, lipidated or conjugated to a carrier molecule.

3. The peptide of claim 1, wherein the peptide has an amino acid residue in the D-enantiomeric form.

4. The peptide of claim 1, wherein the amino acid sequence consists of SEQ ID NO:14.

5. The peptide of claim 4, wherein the peptide is SEQ ID NO:1.

6. The peptide of claim 1, wherein the amino acid sequence consists of SEQ ID NO:15.

7. The peptide of claim 6, wherein the peptide is SEQ ID NO:2.

8. A composition comprising a peptide according to claim 1, and a pharmaceutically acceptable carrier.

9. The composition of claim 8, wherein the peptide is present in a concentration ranging from about 0.1 µg/mL to about 50 µg/mL.

10. The composition of claim 8, wherein the composition further comprises a protease inhibitor.

11. The composition of claim 8, wherein the composition is in the form of an aerosol, emulsion, liquid, lotion, cream, paste, ointment, powder, or foam.

12. The composition of claim 8, wherein the peptide is SEQ ID NO:1 or SEQ ID NO:2.

13. A method for treating inflammation in a mammal, the method comprising administering to a site of inflammation of said mammal a therapeutically effective amount of the composition according to claim 8 for an effective amount of time.

14. The method of claim 13, wherein said inflammation is located in the skin or associated mucosal tissue of said mammal.

15. The method of claim 14, wherein said inflammation is located in skin and is due to exposure to ultraviolet radiation.

16. The method of claim 15, wherein the peptide of the composition is SEQ ID NO:1 or SEQ ID NO:2.

17. The method of claim 14, wherein the inflammation site is an abrasion, blister, burn, laceration, ulcer, bruise, rash or scar.

18. The method of claim 13, wherein the peptide of the composition is SEQ ID NO:1 or SEQ ID NO:2.

19. The method of claim 13, wherein the therapeutically effective amount of the composition comprises peptide at a concentration ranging from about 0.1 µg/mL to about 50 µg/mL.

20. The method of claim 13, wherein the composition further comprises a protease inhibitor.

* * * * *

```
                        SEQUENCE LISTING

<160> NUMBER OF SEQ ID NOS: 22

<210> SEQ ID NO 1
<211> LENGTH: 4
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (4)..(4)
<223> OTHER INFORMATION: Amino acid residue is modified to contain an
      amino group

<400> SEQUENCE: 1

Pro Gln Glu Lys
1

<210> SEQ ID NO 2
<211> LENGTH: 4
<212> TYPE: PRT
<213> ORGANISM: Artificial sequence
<220> FEATURE:
<223> OTHER INFORMATION: Synthetic
<220> FEATURE:
<221> NAME/KEY: MOD_RES
<222> LOCATION: (4)..(4)
<223> OTHER INFORMATION: Amino acid residue is modified to contain an
      amino group

<400> SEQUENCE: 2

Pro Gln Glu Ile
1

<210> SEQ ID NO 3
<211> LENGTH: 4
<212> TYPE: PRT
<213> ORGANISM: Artificial sequence
<220> FEATURE:
<223> OTHER INFORMATION: Synthetic
<220> FEATURE:
<221> NAME/KEY: MOD_RES
<222> LOCATION: (4)..(4)
<223> OTHER INFORMATION: Amino acid residue is modified to contain an
      amino group

<400> SEQUENCE: 3

Pro Gln Glu Met
1
```

```
<210> SEQ ID NO 4
<211> LENGTH: 4
<212> TYPE: PRT
<213> ORGANISM: Artificial sequence
<220> FEATURE:
<223> OTHER INFORMATION: Synthetic
<220> FEATURE:
<221> NAME/KEY: MOD_RES
<222> LOCATION: (4)..(4)
<223> OTHER INFORMATION: Amino acid residue is modified to contain an
      amino group

<400> SEQUENCE: 4

Pro Thr Glu Asp
1

<210> SEQ ID NO 5
<211> LENGTH: 4
<212> TYPE: PRT
<213> ORGANISM: Artificial sequence
<220> FEATURE:
<223> OTHER INFORMATION: Synthetic
<220> FEATURE:
<221> NAME/KEY: MOD_RES
<222> LOCATION: (4)..(4)
<223> OTHER INFORMATION: Amino acid residue is modified to contain an
      amino group

<400> SEQUENCE: 5

Pro Gly Glu Asp
1

<210> SEQ ID NO 6
<211> LENGTH: 4
<212> TYPE: PRT
<213> ORGANISM: Artificial sequence
<220> FEATURE:
<223> OTHER INFORMATION: Synthetic
<220> FEATURE:
<221> NAME/KEY: MOD_RES
<222> LOCATION: (4)..(4)
<223> OTHER INFORMATION: Amino acid residue is modified to contain an
      amino group

<400> SEQUENCE: 6

Pro Leu Glu Val
1

<210> SEQ ID NO 7
<211> LENGTH: 4
<212> TYPE: PRT
<213> ORGANISM: Artificial sequence
<220> FEATURE:
<223> OTHER INFORMATION: Synthetic
<220> FEATURE:
<221> NAME/KEY: MOD_RES
<222> LOCATION: (4)..(4)
<223> OTHER INFORMATION: Amino acid residue is modified to contain an
      amino group

<400> SEQUENCE: 7

Pro Gln Glu Asn
1

<210> SEQ ID NO 8
<211> LENGTH: 4
<212> TYPE: PRT
<213> ORGANISM: Artificial sequence
<220> FEATURE:
<223> OTHER INFORMATION: Synthetic
<220> FEATURE:
```

```
<221> NAME/KEY: MOD_RES
<222> LOCATION: (4)..(4)
<223> OTHER INFORMATION: Amino acid residue is modified to contain an
      amino group

<400> SEQUENCE: 8

Pro Val Glu Ser
1

<210> SEQ ID NO 9
<211> LENGTH: 4
<212> TYPE: PRT
<213> ORGANISM: Artificial sequence
<220> FEATURE:
<223> OTHER INFORMATION: Synthetic
<220> FEATURE:
<221> NAME/KEY: MOD_RES
<222> LOCATION: (4)..(4)
<223> OTHER INFORMATION: Amino acid residue is modified to contain an
      amino group

<400> SEQUENCE: 9

Pro Glu Glu Ser
1

<210> SEQ ID NO 10
<211> LENGTH: 4
<212> TYPE: PRT
<213> ORGANISM: Artificial sequence
<220> FEATURE:
<223> OTHER INFORMATION: Synthetic
<220> FEATURE:
<221> NAME/KEY: MOD_RES
<222> LOCATION: (4)..(4)
<223> OTHER INFORMATION: Amino acid residue is modified to contain an
      amino group

<400> SEQUENCE: 10

Pro Val Glu Thr
1

<210> SEQ ID NO 11
<211> LENGTH: 4
<212> TYPE: PRT
<213> ORGANISM: Artificial sequence
<220> FEATURE:
<223> OTHER INFORMATION: Synthetic
<220> FEATURE:
<221> NAME/KEY: MOD_RES
<222> LOCATION: (4)..(4)
<223> OTHER INFORMATION: Amino acid residue is modified to contain an
      amino group

<400> SEQUENCE: 11

Pro Glu Glu Thr
1

<210> SEQ ID NO 12
<211> LENGTH: 4
<212> TYPE: PRT
<213> ORGANISM: Artificial sequence
<220> FEATURE:
<223> OTHER INFORMATION: Synthetic
<220> FEATURE:
<221> NAME/KEY: MOD_RES
<222> LOCATION: (4)..(4)
<223> OTHER INFORMATION: PPEN

<400> SEQUENCE: 12

Pro Pro Glu Asn
1
```

```
<210> SEQ ID NO 13
<211> LENGTH: 4
<212> TYPE: PRT
<213> ORGANISM: Artificial sequence
<220> FEATURE:
<223> OTHER INFORMATION: Synthetic
<220> FEATURE:
<221> NAME/KEY: MOD_RES
<222> LOCATION: (4)..(4)
<223> OTHER INFORMATION: Amino acid residue is modified to contain an
      amino group

<400> SEQUENCE: 13

Pro Thr Glu Asn
1

<210> SEQ ID NO 14
<211> LENGTH: 4
<212> TYPE: PRT
<213> ORGANISM: Artificial sequence
<220> FEATURE:
<223> OTHER INFORMATION: Synthetic

<400> SEQUENCE: 14

Pro Gln Glu Lys
1

<210> SEQ ID NO 15
<211> LENGTH: 4
<212> TYPE: PRT
<213> ORGANISM: Artificial sequence
<220> FEATURE:
<223> OTHER INFORMATION: Synthetic

<400> SEQUENCE: 15

Pro Gln Glu Ile
1

<210> SEQ ID NO 16
<211> LENGTH: 6
<212> TYPE: PRT
<213> ORGANISM: Artificial sequence
<220> FEATURE:
<223> OTHER INFORMATION: Synthetic
<220> FEATURE:
<221> NAME/KEY: MOD_RES
<222> LOCATION: (2)..(5)
<223> OTHER INFORMATION: X = any amino acid residue
<220> FEATURE:
<221> NAME/KEY: MOD_RES
<222> LOCATION: (6)..(6)
<223> OTHER INFORMATION: X = aromatic or acidic amino acid residue

<400> SEQUENCE: 16

Pro Xaa Glu Xaa Xaa Xaa
1               5

<210> SEQ ID NO 17
<211> LENGTH: 15
<212> TYPE: PRT
<213> ORGANISM: Artificial sequence
<220> FEATURE:
<223> OTHER INFORMATION: Synthetic
<220> FEATURE:
<221> NAME/KEY: MOD_RES
<222> LOCATION: (15)..(15)
<223> OTHER INFORMATION: Amino acid residue is modified to contain an
      amino group

<400> SEQUENCE: 17
```

```
Phe Ala Lys Ala Leu Lys Ala Leu Leu Lys Ala Leu Lys Ala Leu
1               5                   10                  15

<210> SEQ ID NO 18
<211> LENGTH: 6
<212> TYPE: PRT
<213> ORGANISM: Artificial sequence
<220> FEATURE:
<223> OTHER INFORMATION: Synthetic
<220> FEATURE:
<221> NAME/KEY: MOD_RES
<222> LOCATION: (6)..(6)
<223> OTHER INFORMATION: Amino acid residue is modified to contain an
      amino group

<400> SEQUENCE: 18

Phe Ala Leu Leu Lys Leu
1               5

<210> SEQ ID NO 19
<211> LENGTH: 6
<212> TYPE: PRT
<213> ORGANISM: Artificial sequence
<220> FEATURE:
<223> OTHER INFORMATION: Synthetic
<220> FEATURE:
<221> NAME/KEY: MOD_RES
<222> LOCATION: (1)..(1)
<223> OTHER INFORMATION: Amino acid residue is modified to contain a
      decanoyl group
<220> FEATURE:
<221> NAME/KEY: MOD_RES
<222> LOCATION: (6)..(6)
<223> OTHER INFORMATION: Amino acid residue is modified to contain an
      amino group

<400> SEQUENCE: 19

Lys Phe Lys Trp Pro Trp
1               5

<210> SEQ ID NO 20
<211> LENGTH: 37
<212> TYPE: PRT
<213> ORGANISM: Artificial sequence
<220> FEATURE:
<223> OTHER INFORMATION: Synthetic

<400> SEQUENCE: 20

Leu Leu Gly Asp Phe Phe Arg Lys Ser Lys Glu Lys Ile Gly Lys Glu
1               5                   10                  15

Phe Lys Arg Ile Val Gln Arg Ile Lys Asp Phe Leu Arg Asn Leu Val
            20                  25                  30

Pro Arg Thr Glu Ser
        35

<210> SEQ ID NO 21
<211> LENGTH: 4
<212> TYPE: PRT
<213> ORGANISM: Artificial sequence
<220> FEATURE:
<223> OTHER INFORMATION: Synthetic

<400> SEQUENCE: 21

Ala Leu Leu Lys
1

<210> SEQ ID NO 22
<211> LENGTH: 19
```

```
<212> TYPE: PRT
<213> ORGANISM: Artificial sequence
<220> FEATURE:
<223> OTHER INFORMATION: Synthetic

<400> SEQUENCE: 22

Arg Ile Val Gln Arg Ile Lys Asp Phe Leu Arg Asn Leu Val Pro Arg
1               5                   10                  15

Thr Glu Ser
```